(12) United States Patent
Patton et al.

(10) Patent No.: US 9,334,281 B2
(45) Date of Patent: *May 10, 2016

(54) FLUOROCHROMES FOR ORGANELLE TRACING AND MULTI-COLOR IMAGING

(75) Inventors: Wayne Forrest Patton, Dix Hills, NY (US); Praveen Pande, Holbrook, NY (US); Yuejun Xiang, Bayside, NY (US); Zaiguo Li, Fresh Meadows, NY (US); James J. Donegan, Long Beach, NY (US); Elazar Rabbani, New York, NY (US)

(73) Assignee: ENZO LIFE SCIENCES, INC., New York, NY (US)

( * ) Notice: Subject to any disclaimer, the term of this patent is extended or adjusted under 35 U.S.C. 154(b) by 921 days.

This patent is subject to a terminal disclaimer.

(21) Appl. No.: 12/231,988

(22) Filed: Sep. 8, 2008

(65) Prior Publication Data

US 2010/0062429 A1    Mar. 11, 2010

(51) Int. Cl.
| | |
|---|---|
| C07C 211/61 | (2006.01) |
| C07D 487/06 | (2006.01) |
| C07C 225/34 | (2006.01) |
| C07C 225/36 | (2006.01) |
| C07C 229/18 | (2006.01) |
| C07C 335/20 | (2006.01) |
| C07D 213/74 | (2006.01) |
| C07D 295/135 | (2006.01) |
| C07F 9/53 | (2006.01) |
| C07F 9/6503 | (2006.01) |
| C09B 1/00 | (2006.01) |
| C09B 1/51 | (2006.01) |
| C09B 1/515 | (2006.01) |
| C40B 40/04 | (2006.01) |
| G01N 33/50 | (2006.01) |

(52) U.S. Cl.
CPC ............ *C07D 487/06* (2013.01); *C07C 225/34* (2013.01); *C07C 225/36* (2013.01); *C07C 229/18* (2013.01); *C07C 335/20* (2013.01); *C07D 213/74* (2013.01); *C07D 295/135* (2013.01); *C07F 9/5304* (2013.01); *C07F 9/65038* (2013.01); *C09B 1/005* (2013.01); *C09B 1/51* (2013.01); *C09B 1/512* (2013.01); *C09B 1/5155* (2013.01); *C40B 40/04* (2013.01); *G01N 33/5005* (2013.01); *G01N 33/5011* (2013.01); *C07C 2103/24* (2013.01)

(58) Field of Classification Search
None
See application file for complete search history.

(56) References Cited

U.S. PATENT DOCUMENTS

| | | |
|---|---|---|
| 2,195,462 A | 4/1940 | Krause |
| 3,792,968 A | 2/1974 | Rickenbacher et al. |
| 3,823,169 A | 7/1974 | Staub |
| 4,868,103 A | 9/1989 | Stavrianopoulos et al. |
| 5,118,801 A | 6/1992 | Lizardi et al. |
| 5,210,015 A | 5/1993 | Gelfand et al. |
| 5,338,854 A | 8/1994 | Kang et al. |
| 5,401,847 A | 3/1995 | Glazer et al. |
| 5,459,268 A | 10/1995 | Haugland et al. |
| 5,491,084 A | 2/1996 | Chalfie et al. |
| 5,538,848 A | 7/1996 | Livak et al. |
| 5,580,990 A | 12/1996 | Van Den Berg et al. |
| 5,625,048 A | 4/1997 | Tsien et al. |
| 5,646,264 A | 7/1997 | Glazer et al. |
| 5,686,261 A | 11/1997 | Zhang et al. |
| 5,777,079 A | 7/1998 | Tsien et al. |
| 5,800,996 A | 9/1998 | Lee et al. |
| 5,804,387 A | 9/1998 | Cormack et al. |
| 5,852,191 A | 12/1998 | Karandikar et al. |
| 5,869,689 A | 2/1999 | Zhang et al. |
| 5,925,517 A | 7/1999 | Tyagi et al. |
| 5,968,738 A | 10/1999 | Anderson et al. |
| 5,981,747 A | 11/1999 | Mujumdar et al. |
| 5,994,056 A | 11/1999 | Higuchi et al. |
| 5,994,077 A | 11/1999 | Valdivia et al. |
| 6,004,536 A | 12/1999 | Leung et al. |
| 6,008,373 A | 12/1999 | Waggoner et al. |
| 6,022,944 A | 2/2000 | Weaver et al. |
| 6,027,881 A | 2/2000 | Pavlakis et al. |
| 6,054,321 A | 4/2000 | Tsien et al. |
| 6,066,476 A | 5/2000 | Tsien et al. |
| 6,077,707 A | 6/2000 | Tsien et al. |
| 6,090,919 A | 7/2000 | Cormack et al. |
| 6,124,128 A | 9/2000 | Tsien et al. |
| 6,133,445 A | 10/2000 | Waggoner et al. |
| 6,140,500 A | 10/2000 | Yan et al. |
| 6,146,826 A | 11/2000 | Chalfie et al. |
| 6,172,188 B1 | 1/2001 | Thastrup et al. |
| 6,174,670 B1 | 1/2001 | Wittwer et al. |

(Continued)

FOREIGN PATENT DOCUMENTS

| | | | | |
|---|---|---|---|---|
| WO | WO2006031719 | * | 3/2006 | ............ A61K 31/33 |
| WO | WO2008/037394 | | 4/2008 | |

OTHER PUBLICATIONS

He, Ling et al. Huaxi Yike Daxue Yaoxueyuan, 1999, 14(4), 221-224 (Derwent Abstract).*

Krapcho, A et al. Bulletin of the Chemical Society of Ethiopia (1988), 2(2), 69-72.*

Winkelmann et al. "Chemotherapeutically Active Anthraquinones. II. Aminomethylantraquinones", Arzneimittel-Forschung (1986), 36(2), 234-247.*

Winkelmann et al. "Chemotherapeutically Active Anthraquinones. II. Aminomethylantraquinones", Arzneimittel-Forschung, 1986; 36(2), 234-247.*

(Continued)

*Primary Examiner* — Clinton Brooks

(74) *Attorney, Agent, or Firm* — Paul Diamond, Esq.

(57) ABSTRACT

Provided are compounds, methods and kits for identifying in cells of interest organelles including nuclei and a wide variety of organelles other than nuclei (non-nuclear organelles), as well as cell regions or cell domains. These compounds and methods can be used with other conventional detection reagents for identifying the location or position or quantity of organelles and even for distinguishing between organelles in cells of interest.

6 Claims, 10 Drawing Sheets

(56) References Cited

U.S. PATENT DOCUMENTS

| | | |
|---|---|---|
| 6,291,203 B1 | 9/2001 | Poot et al. |
| 6,468,753 B1 | 10/2002 | Smith et al. |
| 6,593,465 B1 | 7/2003 | Wolff et al. |
| 6,664,047 B1 | 12/2003 | Haugland et al. |
| 6,686,145 B1 | 2/2004 | Waggoner et al. |
| 6,969,597 B2 | 11/2005 | Lukyanov et al. |
| 7,060,427 B2 | 6/2006 | Smith et al. |
| 7,150,979 B2 | 12/2006 | Lukyanov et al. |
| 7,157,565 B2 | 1/2007 | Lukyanov et al. |
| 7,166,444 B2 | 1/2007 | Lukyanov et al. |
| 7,183,399 B2 | 2/2007 | Lukyanov et al. |
| 7,297,782 B2 | 11/2007 | Labas et al. |
| 2002/0077366 A1 | 6/2002 | Banerjee et al. |
| 2003/0225247 A1 | 12/2003 | Stavrianopoulos et al. |
| 2005/0054006 A1 | 3/2005 | Chang et al. |
| 2005/0137388 A1 | 6/2005 | Rabbani et al. |
| 2007/0111251 A1 | 5/2007 | Rosania et al. |
| 2008/0166749 A1 | 7/2008 | Cubitt |
| 2010/0062429 A1 | 3/2010 | Patton et al. |
| 2010/0062460 A1 | 3/2010 | Pande et al. |

OTHER PUBLICATIONS

Bassoe et al., Investigations of Phagosomes, Mitochondria, and Acidic Granules in Human Neutrophils Using Fluorescent Probes, Cytometry Part B (Clinical Cytometry) 2003, 21-29, 51B.

Boldyrev et al., New BODIPY lipid probes for fluorescence studies of membranes, J Lipid Res. 2007,1518-1532, 48.

Rashid et al., Predicting the behaviour and selectivity of fluorescent probes for lysosomes and related structures by means of structure-activity models, Histochemical Journal 1991, 450-459, 23.

Deng et al., Fluorescent Conjugates of Brefeldin A Selectively Stain the Endoplasmic Reticulum and Golgi Complex of Living Cells, J Histochem Cytochem 1995, 907-915, 43.

Diwu et al., A novel acidotropic pH indicator and its potential application in labeling acidic organelles of live cells, Chemistry & Biology, 1999, 411-418, 6.

Freundt et al., Photoconversion of Lysotracker Red to a green fluorescent molecule, Cell Research 2007, 956-958, 17.

Johnson et al., Self-association of Glucagon As Measured by the Optical Properties of Rhodamine 6G*, The Journal of Biological Chemistry, 1973, 1353-1356, 253.

Lee et al., Development of novel cell-permeable DNA sensitive dyes using combinatorial synthesis and cell-based screening, Chem. Commun., 2003, 1852-1853.

Li et al., Synthesis and Spectral Properties of Cholesterol- and FTY720-Containing Boron Dipyrromethene Dyes, J Org Chem. 2007, 8376-8382, 72.

Nadrigny et al., Systematic Colocalization Errors between Acridine Orange and EGFP in Astrocyte Vesicular Organelles, Biophysical Journal, 2007 969-980, 93.

Pagano et al., Molecular Trapping of a Fluorescent Ceramide Analogue at the Golgi Apparatus of Fixed Cells: Interaction with Endogenous Lipids Provides a trans-Golgi Marker for Both Light and Electron Microscopy, The Journal of Cell Biology 1989, 2067-2079, 109.

Pagano et al., A Novel Fluorescent Ceramide Analogue for Studying Membrane Traffic in Animal Cells: Accumulation at the Golgi Apparatus Results in Altered Spectral Properties of the Sphingolipid Precursor, The Journal of Cell Biology 1991, 1267-1279, 113.

Poot et al., Analysis of Mitochondrial Morphology and Function with Novel Fixable Fluorescent Stains, The Joournal of Histochemistry and Cytochemistry, 1996,1363-1372, 44.

Rosania et al., Combinatorial Approach to Organelle-Targeted Fluorescent Library Based on the Styryl Scaffold, J Am Chem. Soc, 2003, 1130-1131, 125.

Rutledge et al., Direct Visualization of Lipid Deposition and Reverse Lipid Transport in a Perfused Artery Roles of VLDL and HDL, Circ Res. 2000, 768-773, 86.

Smith et al., Characteristics of a Novel Deep Red/Infrared Fluorescent Cell-Permeant DNA Probe, DRAQ5, in Intact Human Cells Analyzed by Flow Cytometry, Confocal and Multiphoton Microscopy, Cytometry 2000, 280-291, 40.

Smith et al., A novel cell permeant and far red-fluorescing DNA probe, DRAQ5, for blood cell discrimination by flow cytometry, Journal of Immunological Methods 1999,131-139, 229.

Snyder et al., Decreased uptake of bodipy-labelled compounds in the presence of the nuclear stain, DRAQ5, Journal of Microscopy, 2003, 208-211, 211.

Zal et al., Spectral Shift of Fluorescent Dye FM4-64 Reveals Distinct Microenvironment of Nuclear Envelope in Living Cells, Traffic 2006,1607-1613, 7.

Zeigler et al., Prenatal diagnosis of Krabbe disease using a fluorescent derivative of galactosylceramide, Clinica Chimica Acta 1984, 313-318, 142.

Zhang et al., A simple statistical parameter for use in evaluation and validation of high throughput screening assays, J Biomol. Screen. 1999, 67-73, 4.

Zhang et al., Small molecule regulators of autophagy identified by an image-based high-throughput screen, PNAS, 2007, 19023-19028, 104.

Zhang et al., Structure of the yeast vacuolar ATPase, J. Biol. Chem. 2008, 35983-35995, 283.

Albay et al., Chloroquine-induced lipidosis mimicking Fabry disease, Modern Pathology 2005, 733-738, 18.

Almela et al., Characterization of the phospholipidogenic potential of 4(1H)-pyridone antimalarial derivatives, Toxicology in Vitro 2009, 1528-1534, 23.

Anderson et al., Drug-induced phospholipidosis, FEBS Letters 2006, 5533-5540, 580.

Baciu et al., Degradative transport of cationic amphiphilic drugs across phospholipid bilayers, Phil. Trans. R. Soc. A 2006, 2597-2614, 364.

Ballabio et al., Lysosomal disorders: From storage to cellular damage, Biochimica et Biophysica Acta 2009, 684-696, 1793.

Bondok et al., Fluorescence histochemical study of the localisation and distribution of beta-adrenergic receptor sites in the spinal cord and cerebellum of the chicken, J. Anat. 1988, 167-174, 160.

Cornett et al., 9-AAP, a Fluorescent Beta-Adrenergic Antagonist, Enters the Hamster Sperm Acrosome in a Manner Inconsistent With Binding to Beta-Adrenergic Receptors, The Journal of Histochemistry and Cytochemistry 1980 462-464, 28.

Cox, T.M., Biomarkers in lysosomal storage diseases: a review, Acta Pmdiatrica, 2005, 39-42, 94(Suppl 447).

Dickens et al., Antioxidant and Lysosomotropic Properties of Acridine-propranolol: Protection against Oxidative Endothelial Cell Injury, J Mol Cell Cardiol 2002, 129-137, 34.

Gatt et al., A Fluorometric Determination of Sphingomyelinase by Use of Fluorescent Derivatives of Sphingomyelin, and its Application to Diagnosis of Niemann-Pick Disease, Clin. Chem. 1980, 93-96, 26/1.

Ikeda et al., Drug-induced phospholipidosis is caused by blockade of mannose 6-phosphate receptor-mediated targeting of lysosomal enzymes, Biochemical and Biophysical Research Communications 2008, 268-274, 377.

Invitrogen, HCS LipidTOX™ Phospholipidosis Detection Reagents, Sep. 2006, MP 34350.

Ishiguro et al., Novel application of 4-nitro-7-(1-piperazinyl)-2,1,3-benzoxadiazole to visualize lysosomes in live cells, BioTechniques 2008, 465-468, 45.

Lemieux et al., Quantitation of the lysosomotropic character of cationic amphiphilic drugs using the fluorescent basic amine Red DND-99, Analytical Biochemistry 2004, 247-251, 327.

Maloteaux et al., Trapping of Labelled Ligands in Intact Cells: a Pitfall in Binding Studies, Biochemical Pharmacology 1983, 2543-2548, 32.

Muller-Hocker et al., Chloroquine-Induced Phospholipidosis of the Kidney Mimicking Fabry's Disease: Case Report and Review of the Literature, Hum Pathol 2003, 285-289, 34.

Raben et al., Monitoring Autophagy in Lysosomal Storage Disorders, Methods Enzymol. 2009, 417-449, 453.

Vibet et al., Differential Subcellular Distribution of Mitoxantrone in Relation to Chemosensitization in Two Human Breast Cancer Cell Lines, Drug Metabolism and Disposition 2007, 822-828, 35.

(56) References Cited

OTHER PUBLICATIONS

Bhandari et al., Phospholipidosis Assay in HepG2 Cells and Rat or Rhesus Hepatocytes Using Phospholipid Probe NBD-PE, Assay and Drug Development Technologies 2008, 407-419, 6.
Casartelli et al., A cell-based approach for the early assessment of the phospholipidogenic potential in pharmaceutical research and drug development, Cell Biology and Toxicology 2003, 161-176,19.
Cramb, Gordon, Selective lysosomal uptake and accumulation of the beta-adrenergic antagonist propranolol in cultured and isolated cell systems, Biochemical Pharmacology 1986, 1365-1372, 35.
Cramer et al., Cytotoxicity and lamellar body induction potential of a racemic benzamide antiarrhythmic compound and enantiomers in cultured rat hepatocytes, Toxic. in Vitro 1994,1083-1090, 8.
Diez-Blanco et al., Isolation, characterization and phospholipid composition of lamellar bodies and subcellular fractions from dog lung, Int. J. Biochem. 1987, 693-698, 19.
Fujimura et al., Cell-based fluorescence assay for evaluation of new-drugs potential for phospholipidosis in an early stage of drug development, Experimental and Toxicologic Pathology 2007, 375-382, 58.
Gum et al., Analysis of two matrix metalloproteinase inhibitors and their metabolites for induction of phospholipidosis in rat and human hepatocytes, Biochemical Pharmacology 2001,1661-1673, 62.
Hjelmeland et al., SB-431542, a small molecule transforming growth factor-beta-receptor antagonist, inhibits human glioma cell line proliferation and motility, Mol Cancer Ther 2004, 737-745, 3.
Kasahara et al., Establishment of an In Vitro High-Throughput Screening Assay for Detecting Phospholipidosis-Inducing Potential, Toxicological Sciences 2006, 133-141, 90.
Morelli et al., Validation of an in vitro screen for phospholipidosis using a high-content biology platform, Cell Biology and Toxicology 2006; 15-27, 22.
Natalie et al., A 96-well flow cytometric screening assay for detecting in vitro phospholipidosis-induction in the drug discovery phase, Toxicology in Vitro 2009, 217-226, 23.
Nioi et al., In Vitro Detection of Drug-Induced Phospholipidosis Using Gene Expression and Fluorescent Phospholipid-Based Methodologies, Toxicological Sciences 2007, 162-173, 99.
Lee et al., DEVDase detection in intact apoptotic cells using the cell permeant fluorogenic substrate, (z-DEVD)2-cresyl violet, Biotechniques 2003, 1080-1085, 35.
Sanchez et al., Amiodarone and Bepridil Inhibit Anthrax Toxin Entry into Host Cells, Antimicrobial Agents and Chemotherapy, 2007, 2403-2411, 51.
Seglen et al., 3-Methyladenine: Specific inhibitor of autophagic/lysosomal protein degradation in isolated rat hepatocytes, Proc. Natl. Acad. Sci. USA, 1982, 1889-1892, 79.
Xu et al., Berbamine: A novel inhibitor of bcr/abl fusion gene with potent anti-leukemia activity, Leukemia Research 2006, 17-23, 30.
Yamamoto et al., Bafilomycin A1 Prevents Maturation of Autophagic Vacuoles by Inhibiting Fusion between Autophagosomes and Lysosomes in Rat Hepatoma Cell Line, H-4-II-E Cells, Cell Structure and Function 1998, 33-42, 23.
Bracamonte et al., Iatrogenic phospholipidosis mimicking Fabry disease, Am. J. Kidney Diseases 2006, 844-850, 48.
Ulrich et al., Potential to induce lamellar bodies and acute cytotoxicity of 6'-alkyl analogues of spectinomycin in primary cultures of rat hepatocyes, Toxic. in Vitro, 1991, 239-245, 5.
Nioi et al., Monitoring the Accumulation of Fluorescently Labeled Phospholipids in Cell Cultures Provides an Accurate Screen for Drugs that Induce Phospholipidosis, Drug and Chemical Toxicology 2008, 515-528, 31.
Tomizawa et al., Physicochemical and cell-based approach for early screening of phospholipidosis-inducing potential, Journal of Toxicological Sciences, 2006, 315-324, 31.
Ulrich et al., An In Vitro Fluorescence Assay for the Detection of Drug-Induced Cytoplasmic Lamellar Bodies, Toxicology Methods 1991, 89-105, 1.
Huange et al., *Bioorg. Med. Chem.*, vol. 13, pp. 1435-1444 (2005).
Mesens et al., "A 96-well flow cytometry screening assay for detecting in vitro phospholipidosis-induction in the drug discovery phase," *Toxicology in Vitro*, vol. 23, pp. 217-226 (2009).
Winkelmann, et al., "Chemotherapeutically Activie Antraquiones," *Drug Res.*, vol. 36, pp. 234-247 (1986).
Zhang et al., "A simple statistical parameter for use in evaluation and validation of high throughput screeing assays," *J. Biomol. Screen*, vol. 4, No. 2, pp. 67-73 (1999).

\* cited by examiner

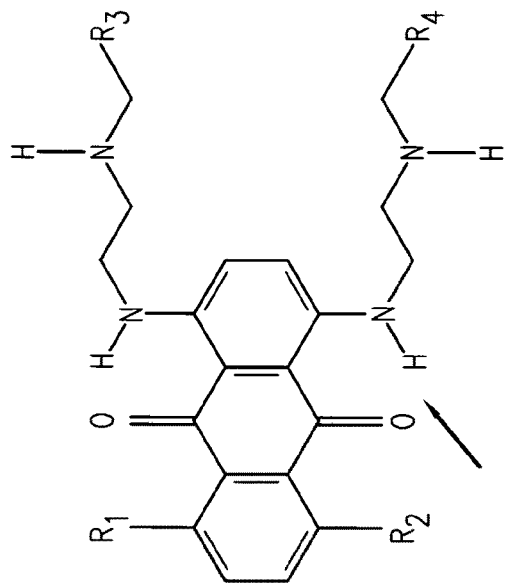
FIG. 1
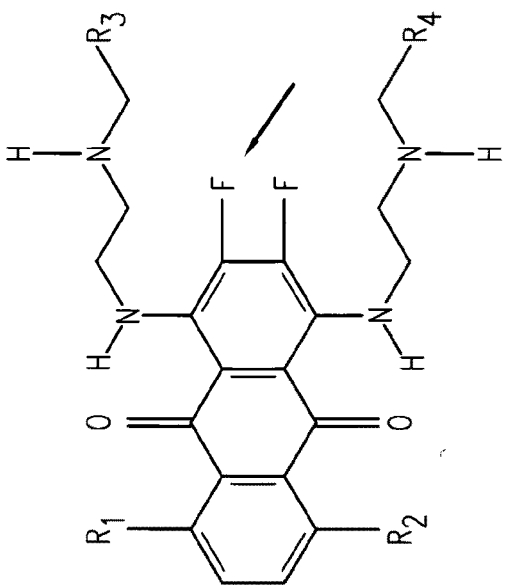
FIG. 2
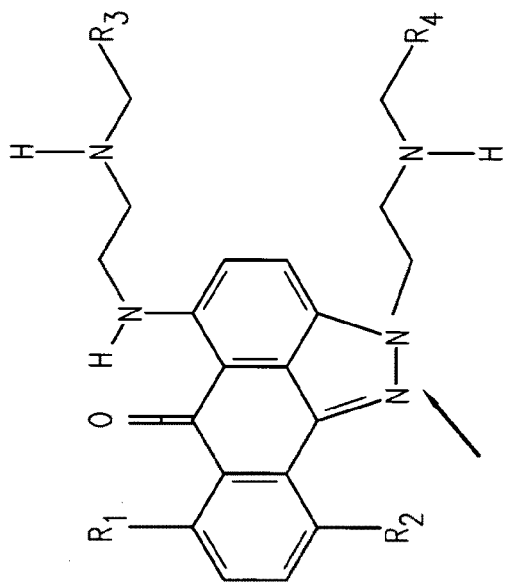
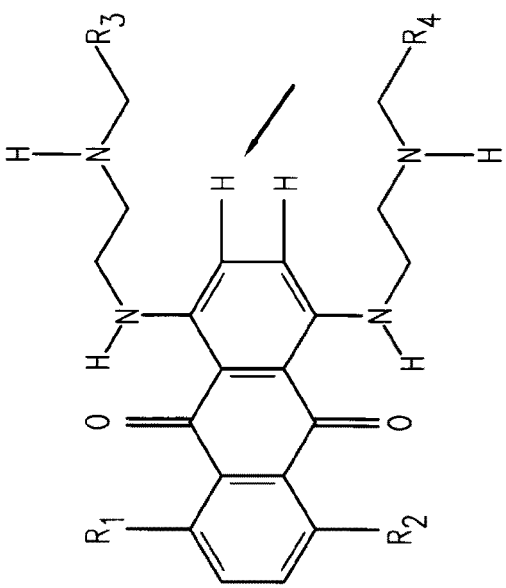

FLUOROCHROMES FOR ORGANELLE TRACING AND MULTI-COLOR IMAGING

FIELD OF THE INVENTION

The invention generally relates to fluorescent dyes suitable for applications involving wide-field fluorescence microscopy, flow cytometry, confocal microscopy, fluorimetry, high-content cell analysis, cell microarray analysis, high-content cell screening, laser-scanning cytometry and other imaging and detection modalities. The invention relates to fluorescent compounds useful for identifying organelles in live and dead cells, including nuclei and organelles other than nuclei (non-nuclear organelles), as well as subcellular organelles, cell domains and cell regions, whether within or on cells, or isolated from cells. In particular, the present invention relates to the identification of subcellular organelles, cell domains, cell regions, and the like, within living cells or extracellularly, with the identifying fluorescent compounds that are retained within or otherwise localize to the specified subcellular organelles, cell domains or cell regions. The fluorescent compounds of the present invention are selectively sequestered in the targeted organelles, domains or regions, rendering them fluorescent and readily identifiable.

All patents, patent applications, patent publications, scientific articles and the like, cited or identified in this application, are hereby incorporated by reference in their entirety in order to describe more fully the state of the art to which the present invention pertains.

BACKGROUND OF THE INVENTION

As genetically encoded reporter molecules, fluorescent proteins have demonstrated applicability and versatility as molecular and cellular probes in life sciences and biomedical research. Among patents relating to fluorescent protein technology are U.S. Pat. Nos. 5,491,084, 5,625,048, 5,777,079, 5,804,387, 5,968,738, 5,994,077, 6,027,881, 6,054,321, 6,066,476, 6,077,707, 6,124,128, 6,090,919, 6,172,188, 6,146,826, 6,969,597, 7,150,979, 7,157,565, 7,166,444, 7,183,399 and 7,297,782, references incorporated herein.

Fluorescent protein fusion to a gene promoter has been employed for reporting or verifying gene expression. Fluorescent protein fusion to a gene of interest has also been used to track a protein as it traverses a cell. If the fusion partner is a structural protein, then information pertaining to cellular architecture may be obtained. Fluorescent proteins have found application in a vast array of experiments, included those relating to monitoring gene promoter activity, gene expression levels, organelle dynamics, cellular architecture, gene expression timing, protein translocation, G-protein-coupled receptor (GPCR) activity, cell lineage, apoptosis, protein degradation, genotoxicity and cytotoxicity.

Cell-based assays are increasingly gaining in popularity in the pharmaceutical industry due to their high physiological relevance. Additional advantages include their ability to predict compound usefulness, evaluate molecular interactions, identify toxicity, distinguish cell type-specific drug effects, and determine drug penetration. Cell-based assays are relevant throughout the drug discovery pipeline, as they are capable of providing data from target characterization and validation to lead identification (primary and secondary screening) to terminal stages of toxicology. Current industry trends of performing drug screening with cell context demand easily monitored, non-invasive reporters. Fluorescent proteins fulfill this demand more completely than any other available tools. Requirements for advanced screening assays are driven by the objective of failing candidate compounds early in the drug discovery pipeline. This fundamental approach increases efficiency, reduces costs, and results in shorter time to market for new drugs. In order to fail compounds early, information-rich data for accurate early-stage decision making is required. Such data may be derived by screening compounds in context, that is, by screening in relevant living systems, rather than with classical biochemical assays, often incorporating sophisticated imaging platforms, such as high-content screening (HCS) workstations. The industrialization of fluorescent microscopy has led to the development of these high-throughput imaging platforms capable of HCS. When coupled with fluorescent protein reporter technology, HCS has provided information-rich drug screens, as well as access to novel types of drug targets.

As industry trends advance toward analysis in living systems (e.g. cells, tissues, and whole organisms), fluorescent proteins, by virtue of their non-invasive, non-destructive properties, are becoming indispensable tools for live-cell analysis. A broad range of fluorescent protein genetic variants are now available, with fluorescence emission profiles spanning nearly the entire visible light spectrum. Mutagenesis efforts in the original jellyfish Aequorea victoria green fluorescent protein have resulted in new fluorescent probes that range in color from blue to yellow and these are some of the most widely used in vivo reporter molecules in biological research today. Longer wavelength fluorescent proteins, emitting in the orange and red spectral regions, have been developed from the marine anemone Discosoma striata and reef corals belonging to the class Anthozoa. Other species have also been mined to produce similar proteins having cyan, green, yellow, orange, red, and even far-red fluorescence emission.

Recent emphasis on multi-color imaging in HCS has created renewed demand for easily measured, non-invasive, and non-disruptive cellular and molecular probes. With the increasingly expanding repertoire of fluorescent proteins has come increased demand for complementary reagents, such as organic fluorochrome counter-stains that augment analysis by providing information relating to co-localization of the fluorescent proteins to various organelles and subcellular targets. To date, however, concerted efforts in developing such organic fluorochromes, specifically tailored to working in concert with fluorescent proteins, has been limited in scope. The application of fluorescent proteins and of organic fluorochromes is not an either/or proposition. Each technology has distinct advantages and limitations. These two technologies can be optimized and combined to work in concert, however, in order to maximize the information content obtained from fluorescence microscopy- and imaging-based screening approaches. By doing so, achieving rich multi-dimensional physiological information can be obtained.

While suitable for analysis of cell surfaces and permeabilized cells, fluorescently-labeled antibodies have few practical applications for intracellular imaging in living cells, due to their inherent inability to penetrate to their targets, which has given rise to development of cell-permeable small molecule organic fluorochromes, certain ones of which naturally sequester inside-specific organelles, based upon biophysical or biochemical properties favoring that distribution. Acceptable small molecule organic probes for cell imaging and analysis need to be minimally perturbing, versatile, stable, easy-to-use, and easy to detect using non-invasive imaging equipment. A problem with the classical organic probes from histology is that many of them require cofactors or, by requiring fixation or staining, report only on the static condition of a dead cell. The required additional steps may be time consuming and expensive and, in the case of fixing and staining, may lack biological relevance. In the context of the analyses described above, an organic probe must be able to report upon events in living cells and in real time. Simplicity is of key importance, especially in the context of drug screening.

While various organic fluorochromes have been developed in the past for live cell analysis, typically they were not devised with optimization of performance in conjunction with the wide palette of available fluorescent proteins in mind. For instance, several U.S. patent documents (U.S. Pat. Nos. 5,338,854, 5,459,268, 5,686,261, 5,869,689, 6,004,536, 6,140,500 and 6,291,203 B1, as well as US Patent Applications 2005/0054006 and 2007/0111251 A1, references incorporated herein) disclose organic fluorochromes which are described as useful for visualizing membranes, mitochondria, nuclei and/or acidic organelles. Additional examples of various fluorochromes and their application in biological imaging may be found in the published literature (see, for example, Pagano et al, 1989; Pagano et al, 1991; Deng et al, 1995; Poot et al, 1996; Diwu et al, 1999; Rutledge et al, 2000; Lee et al, 2003; Bassøe et al, 2003; Rosania et al, 2003; Li et al 2007; Boldyrev et al, 2007; Nadrigny et al, 2007). These dyes have been created using a number of fluorophores, most commonly dipyrrometheneboron difluoride (BODIPY), cyanine, carbocyanine, styryl and diaminoxanthene core structures. Typical emission maxima for these organic fluorophores span from 430 to 620 nm. Many of the dyes consequently occupy valuable regions of the visible emission spectrum that preclude use of various fluorescent proteins. By doing so, their use limits the overall levels of multiplexing achievable in HCS assays. Additionally, these dyes often display other suboptimal properties, such as a propensity to photo-bleach, metachromasy and even a tendency to photo-convert to different emission maxima upon brief exposure to broad-band illumination.

Artifacts Associated with Previously Devised Organic Fluorochromes for Live Cell Analysis Fluorescence co-localization imaging is a powerful method for exploring the targeting of molecules to intracellular compartments and for screening of their associations and interactions. In these kinds of experiments, distinct fluorochromes and/or fluorescent proteins of interest are imaged as spectrally separated detection channels. The fluorescence intensity in each channel is ideally dominated by spatial and concentration information derived from one fluorophore only. Many commercially available organic fluorophores for subcellular analysis are disadvantaged in displaying suboptimal properties relating to these types of applications.

Lysotracker Red DND-99 (Invitrogen, Carlsbad, Calif.) contains a BODIPY fluorophore in the form of a conjugated multi-pyrrole ring structure and also contains a weakly basic amine that causes the fluorochrome to selectively accumulate in acidic compartments, exhibiting red fluorescence upon appropriate illumination (excitation: 577 nm, emission: 590 nm) (Freundt et al, 2007). Lysotracker Red is structurally related to Lysotracker Green but the former has an additional pyrrole ring in conjugation with the primary structure, which produces a longer wavelength emission. Lysotracker Red has commonly been used in multi-color imaging studies as a lysosomal marker to determine intracellular localization of GFP-tagged proteins by fluorescence or confocal microscopy. Excitation of the red-emitting molecule with broadband illumination induces, however, molecular changes rendering its photochemical properties similar to those of Lysotracker Green. The similarities between the spectra of Lysotracker Green and converted Lysotracker Red suggest that the third pyrrole ring is taken out of conjugation during the photo-conversion process, leading to a shorter wavelength dye emission. Thus, Lysotracker Red staining for epifluorescence or confocal microscopy, in conjunction with visualization of GFP, leads to spurious results due to photo-conversion of the fluorophore (Freundt et al, 2007).

Acridine orange (Sigma-Aldrich, Saint Louis, Mo. and other sources) has also been used extensively as a fluorescent probe of lysosomes and other acidic subcellular compartments. Acridine orange's metachromasy results, however, in the concomitant emission of green and red fluorescence from stained cells and tissue (Nadrigny et al, 2007). Evanescent-field imaging with spectral fluorescence detection, as well as fluorescence lifetime imaging microscopy demonstrate that green fluorescent acridine orange monomers inevitably coexist with red fluorescing acridine orange dimers in labeled cells. The green monomer emission spectrally overlaps with that of GFP and produces a false apparent co-localization on dual-color images. Due to its complicated photochemistry and interaction with cellular constituents, acridine orange is a particularly problematic label for multi-color fluorescence imaging-both for dual-band and spectral detection. Extreme caution is required, therefore, when deriving quantitative co-localization information from images of GFP-tagged proteins in cells co-labeled with acridine orange.

In principle, the styryl dye, FM4-64 (Invitrogen, Carlsbad, Calif.) is useful for studying endocytosis and vesicular recycling because it is reputed to be confined to the luminal layer of endocytic vesicles. This particular dye distributes throughout intracellular membranes and it indiscriminately stains both the endoplasmic reticulum and nuclear envelope (Zal et al, 2006). However, though the different pools of dye all emit at roughly 700 nm, a spectral shift in fluorescence excitation maximum is observed wherein the dye present in endocytic vesicles and the endoplasmic reticulum absorbs at 510 nm, while the dye associated with the nuclear matrix absorbs at 622 nm. While this can be used advantageously in order to selectively image the nuclear membrane, in certain multi-parametric imaging experiments the dual absorption properties can be problematic. The shift in peak of the absorption spectrum is not confined to FM dyes. A similar phenomenon has also been reported for Rhodamine 6G, where the dye's absorbance maximum is red-shifted from 527 to 546 nm in a concentration dependent manner (Johnson et al, 1978). Rhodamine 6G is commonly employed to label leukocytes, especially in vascular injury models.

Fluorescent analogs of ceramide are commonly employed to visualize golgi bodies in live cells. The fluorescence emission maximum of certain BODIPY-labeled ceramides, such as $C_5$-DMD-Ceramide (a.k.a. C5-BODIPY-Cer, Invitrogen, Carlsbad, Calif.), has been shown to depend strongly upon the molar density of the probe in the membrane, shifting in emission maximum from green (~515 nm) to red (~620 nm) with increasing concentration (Pagano et al, 1991). Consequently, in live cells, the Golgi bodies display yellow/orange fluorescence emission (a combination of red and green fluorescence emission), whereas predominantly green fluorescence emission is observed in the endoplasmic reticuli, the nuclear envelope and mitochondria. Co-localization studies with GFP are compromised, therefore, when employing these fluorescent ceramide analogs, due to their inherent dual emission characteristics.

Only in the specific instance of nuclear staining have the aforementioned problems been alleviated to a large extent. DRAQ5™ ([1,5-Bis[[2-(dimethylamino)ethyl]amino]4,8-dihydroxyanthracene-9,10-dione], Biostatus Limited, UK) is a cell-permeable substituted anthraquinone dye designed for use in a range of fluorescence detection technologies, for the discrimination of nucleated cells (U.S. Pat. Nos. 6,468,753 B1 and 7,060,427 B2, Smith et al, 1999; 2000). The dye permits nuclear discrimination and functional assays to be performed in live cells in combination with a variety of UV and visible range fluorochromes, such as fluorescein, R-phycoerythrin and the GFP super-family. Additionally, the dye has little propensity to photo-bleach.

SUMMARY OF THE INVENTION

The present invention provides compounds comprising the generalized structure

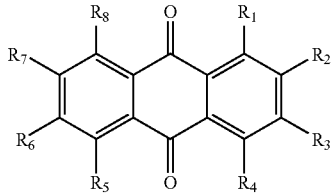

wherein $R_1$-$R_4$ and $R_5$-$R_8$ are independently selected from H, OH, halide, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein at least one of $R_5$-$R_8$ or $R_1$-$R_4$ is (a) a heteroalkyl chain comprising at least one phosphorus, oxygen, sulfur, boron, or selenium atom.

The present invention also provides compounds comprising the generalized structure

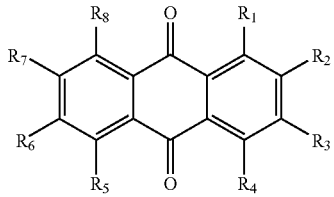

wherein $R_1$-$R_4$ and $R_5$-$R_8$ are independently selected from H, OH, halide, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, and a substituted or unsubstituted amine; and wherein at least one of $R_5$-$R_8$ or $R_1$-$R_4$ comprises thiourea.

This invention additionally provides compounds having the generalized structure

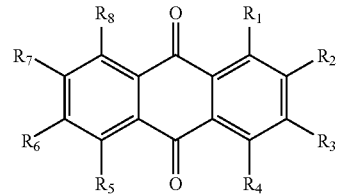

wherein $R_1$-$R_4$ and $R_5$-$R_8$ are independently selected from H, OH, halide, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein only one member of $R_1$-$R_8$ comprises the structure NH-A-$R_aR_b$, wherein A is a $C_{2-8}$ alkylene group and $R_a$ and $R_b$ are independently selected from H, $C_{1-4}$ alkyl, $C_{2-4}$ hydroxyalkyl and $C_{2-4}$ aminoalkyl.

This invention further provides compounds having the generalized structure

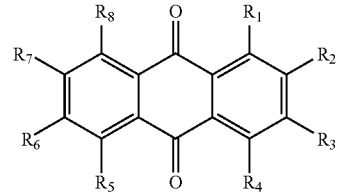

wherein $R_1$-$R_4$ and $R_5$-$R_8$ are independently selected from H, OH, halide, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein at least one member of $R_1$-$R_8$ comprises the structure NH—$R_a$, wherein $R_a$ is cyclic or heterocyclic ring.

Also provided by the present invention are compounds comprising the generalized structure

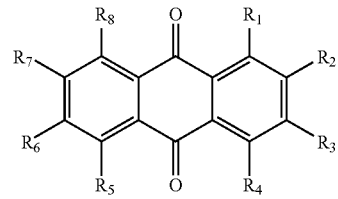

wherein $R_5$-$R_8$ are independently selected from H, OH, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein $R_1$-$R_4$ are independently selected from H, halide, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein at least one of $R_5$-$R_8$ or $R_1$-$R_4$ is an alkyl chain substituted with at least one phosphorus, oxygen, sulfur or selenium.

In another aspect this invention provides compounds comprising the generalized structure

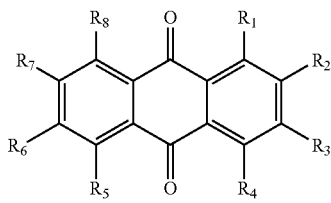

wherein $R_5$-$R_8$ are independently selected from H, OH, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein $R_1$-$R_4$ are independently selected from H, halide, nitro group, CN group, a charged group comprising salts of organic acids, onium groups and protonated amines, wherein said salts of organic acids comprise sulfate, sulfonate, phosphate, phosphonate, carboxylate, borate, and combinations thereof, and wherein said onium groups comprise quaternary ammonium, sulfonium, phosphonium, and combinations thereof, a substituted or unsubstituted alkyl or alkenyl group, a substituted or unsubstituted amine, and a thiourea group; and wherein at least two of $R_1$-$R_8$ comprise a substituted amine.

A further aspect provided by this invention is a multimeric compound comprising two or more of the compounds described above and in further detail below, such multimeric compounds being joined together through a linkage group comprising a substituted or unsubstituted alkyl group, a substituted or unsubstituted alkenyl group, a substituted or unsubstituted heteroalkyl group, a substituted or unsubstituted heteroalkenyl group, and an amide.

This invention further provides methods for identifying organelles and related cellular structures and elements. Among these is a method of identifying the location or position of nuclei within cells of interest comprising the steps of (A) providing (i) the cells of interest; (ii) any of the compositions described above or herein below; (B) incubating the cells of interest (i) with the composition (ii); and (C) identifying the location or position of the nuclei.

Another method provided by this invention is one for identifying within cells of interest the location or position of organelles other than nuclei. This method comprises the steps of (A) providing (i) the cells of interest; (ii) any of the compositions described above or herein below; (B) incubating the cells of interest (i) with the composition (ii); and (C) identifying the location or position of the organelles which are other than nuclei.

Other aspects and embodiments are described in further detail below.

BRIEF DESCRIPTION OF THE FIGURES

FIG. 1: Example of bioisoteric anthraquinone fluorochrome structures emitting in the green and far-red regions of the visible light spectrum.

FIG. 2: Example of bioisoteric anthraquinone fluorochrome structures emitting in the red and far-red regions of the visible light spectrum.

DESCRIPTION OF THE INVENTION

Figure 3:
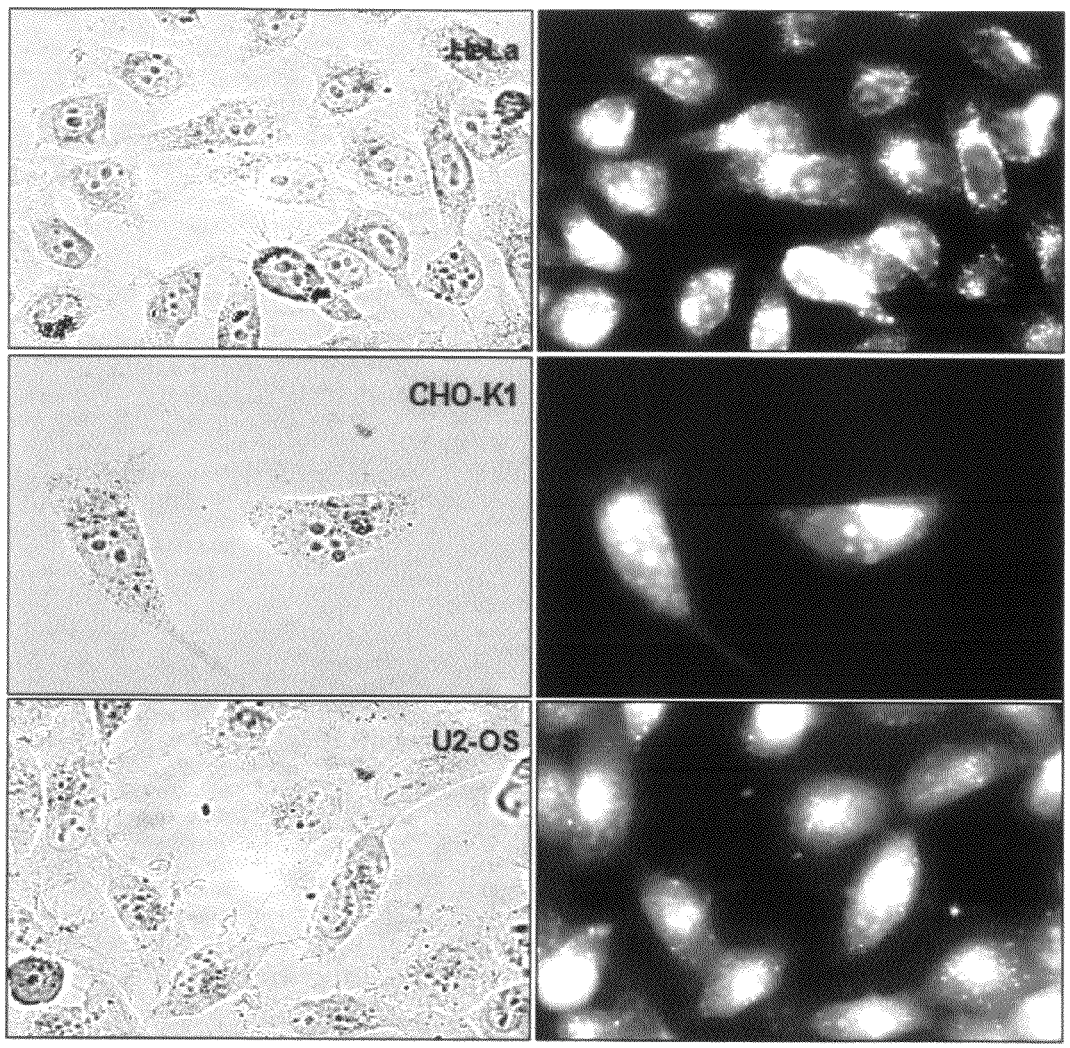
FIG. 3: Staining lysosomes in various live mammalian cells with an anthraquinone fluorochrome.

One of the major challenges in the creation of fluorescent dyes as cell-permeable probes is to generate fluorophores that fluoresce strongly in aqueous media, particularly above 600 nm or at even longer wavelengths. Motivation for research in this area is drawn from needs for intracellular, tissue, and whole organism imaging. The present invention provides a family of far-red emitting cell-permeable small molecule organic probes that spontaneously localize to specific subcellular organelles, cell domains and cell regions which can be readily used in combination with other commonly used UV- and visible excitable organic fluorochromes and fluorescent proteins in multi-color imaging and detection applications. Most importantly, many of the organic probes of the present invention do not occupy valuable regions of the visible emission spectrum utilized by the common UV and visible range fluorochromes and fluorescent proteins, most particularly green fluorescent protein (GFP) and the fluorescent protein super-family. These organic probes can then be used in concert with the other fluorochromes to report drug or compound effects in the dynamic context of the living whole cell.

DEFINITIONS

By fluorescence is meant the emission of light as a result of absorption of light-emission, occurring at a longer wavelength than the incident light.

By fluorophore is meant a component of a molecule which causes a molecule to be fluorescent.

By fluorochrome is meant any of a group of fluorescent dyes used to stain biological specimens.

By anthraquinone is meant the quinone derivative of anthracene, a tricyclic aromatic hydrocarbon containing two opposite carbonyl groups (C═O) at the 9, 10 positions of anthracene. These compounds may also be referred to as anthracenediones or as 9,10-dioxoanthracenes.

By aza-anthraquinone is meant a heterocyclic compound structurally related to anthraquinone, bearing either one (mono-aza) or two (di-aza) nitrogen atom substitutions in the anthracene framework.

By anthrapyrazole is meant a derivative of anthraquinone in which a pyrazole ring is fused to the anthraquinone core structure in order to generate a tetracyclic ring system.

By aza-anthrapyrazole is meant a derivative of aza-anthraquinone in which a pyrazole ring is fused to the aza-anthraquinoine core structure in order to generate a tetracyclic ring system.

By benzophenoxazine is meant a phenoxazine core structure that has been extended through addition of a fused benzene ring. Benzophenoxazines may be 'angular' or 'linear' depending upon the orientation of the ring fusion.

By metachromasy is meant the hypsochromic (shift in absorption to shorter wavelength) and hypochromic (decrease in intensity of emitted fluorescence) change in color exhibited by certain dyes in aqueous-based media under conditions such as: (1), increase in dye concentration; (2), temperature decrease; (3), salting out; and (4), interaction with substrates that favor water intercalation and/or proximity or stacking of dye monomers.

By bioisosterism is meant substituents or groups with similar physical or chemical properties that impart similar biological properties to a chemical compound. The purpose of exchanging one bioisostere for another is to enhance the desired biological or physical properties of a compound without making significant changes in chemical structure.

Basic Fluorophore Core Structures:

The present invention pertains to the preparation and use of fluorescent dyes comprising polycyclic fused ring systems, such as anthraquinone, anthrapyrazole, and benzophenoxazine fluorophores as well as their aza derivatives in cell imaging and detection. Generally, these types of dyes are electrically neutral and lipophilic, properties which permit them to be better solubilized in non-polar environments, such as cell membranes thereby rendering them cell permeable. More particularly, the invention relates to modifications of these dyes with functional groups that target the dyes to various subcellular organelles or regions. In one embodiment of the present invention, the functional groups attached to the dyes do not have a propensity for a particular organelle or region in and of themselves, but their addition to a dye endows the modified dye with such properties. In another embodiment of the present invention, functional groups are added that intrinsically have their own affinity for a particular organelle or region and the addition of such groups to a dye conveys this property to the dye.

In the present invention, the cell-permeable fluorescent dyes may also be described by the following general formulas:

The present invention provides for a dye having the formula:

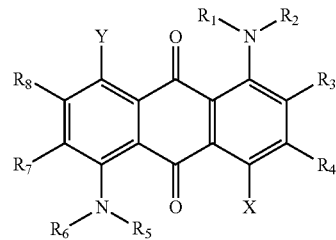

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$, $R_2$, $R_5$ and $R_6$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer. When $R_1=R3=R_4=R_5=R_7=R_8=H$; X and Y are OH, $R_2$ and $R_6$ contain $-L-NR_9R_{10}$, then $R_2=R_6$ and wherein when L is a $C_{2-8}$ alkylene group and $R_9$ and $R_{10}$ are independently selected from hydrogen, $C_{1-4}$ alkyl, $C_{2-4}$ hydroxyl-alkyl and $C_{2-4}$ aminoalkyl or $R_9$ and $R_{10}$ together form a $C_{2-6}$ alkylene group which with the nitrogen atom to which $R_9$ and $R_{10}$ are attached forms a heterocyclic ring.

The present invention also provides for a dye having the formula:

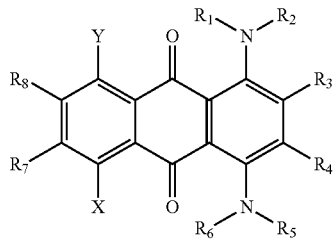

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$, $R_2$, $R_5$ and $R_6$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

The present invention also provides for a dye having the formula:

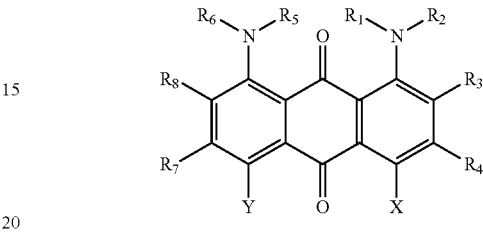

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$, $R_2$, $R_5$ and $R_6$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

The present invention also provides for a dye based on an anthrapyrazole ring having the formula:

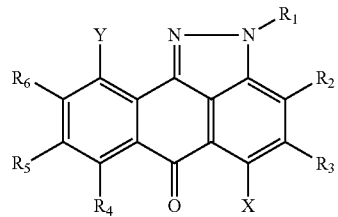

wherein each of X, Y, $R_2$, $R_3$, $R_4$, $R_5$ and $R_6$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl-group is saturated or unsaturated, linear or branched, substituted or unsubstituted, an alkoxy group wherein the alkoxy group is saturated or unsaturated, branched or linear, substituted or unsubstituted. $R_1$ is independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

The present invention also provides a dye based on a bis-anthrapyrazole ring having the formula:

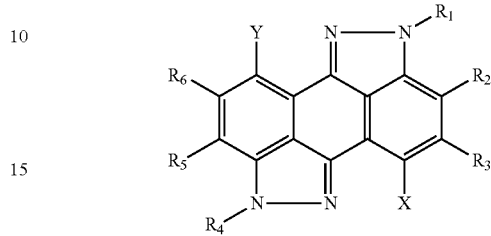

wherein each of X, Y, $R_2$, $R_3$, $R_5$ and $R_6$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$ and $R_4$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

Spectral Properties

In one particular embodiment of the present invention, the preparation of cell-permeable, substituted anthraquinones are described, as well as their applications in a range of fluorescence imaging and detection technologies. Fluorochromes based upon this fluorophore core absorb maximally in the vicinity of 647 nm and emit maximally in the vicinity of 670 nm. These far-red emitting fluorochromes are thus particularly useful in multi-parametric imaging applications using a range of commonly available UV and visible light-excitable fluorochromes and fluorescent proteins. Fluorinated derivatives of this core structure are useful for shifting the excitation/emission profile of the fluorophore from the far-red to the red region of the visible spectrum. Aza-anthraquinones, based upon, for example, a 9(10H)-acridanone or benz[g]isoquinoline-5,10-dione core structure, may also find use in the present invention although the presence of nitrogen atom substitutions in the anthracene framework shifts the fluorescence emission characteristics of the compounds, so as they emit maximally at roughly 400-430 nm. These compounds can find application in multi-color imaging applications, especially in conjunction with turquoise-, green-, red- and far-red-emitting dyes.

This invention further pertains to the preparation and use of other cell-permeable substituted anthrapyrazoles containing carbocyclic or heterocyclic fluorophores. Fluorochromes based upon this fluorophore core absorb maximally in the vicinity of 410 nm and emit maximally in the vicinity of 520 nm. Emission of these fluorophores may also be shifted to shorter wavelengths through addition of fluorine atoms to the core fluorophore structure.

While being green-emitting rather than far red-emitting fluorophores, and thus emitting in a valuable region of the light spectrum overlapping other common green-emitting fluorochromes such as fluorescein and GFP, the anthrapyrazoles have other favorable properties relative to conventional fluorophores, such as BODIPY-FL, most particularly high resistance to photo-bleaching. Nuclear-targeting anthrapyrazoles offer performance advantages relative to blue-emitting dyes, such as DAPI and the Hoescht dyes for live cell imaging since emission that is distinct from intracellular NADH and FADH autofluorescence is achieved and the requirement for specialized UV-emitting laser sources is avoided, especially important in flow cytometry applications.

The green-emitting anthrapyrazoles are also suitable for use in combination with the described red- and far red-emitting anthraquinones of the present invention in multi-parametric analyses. The green- or far red-emitting fluorophores may be used in combination with red-emitting, yellow-emitting and/or blue-emitting fluorochromes or fluorescent proteins for multi-parametric analyses. Fluorescent cell-permeable, substituted benzophenoxazine dyes are also valuable for highlighting subcellular organelles, domains and regions. Benzo[a]phenoxazine, benzo[b]phenoxazine and benzo[c]phenoxazine are all suitable core fluorophore structures for substitution of organelle-targeting groups. Chemical substituents that freely donate and/or accept electron density on benzophenoxazine core structures can, in some orientations, provide fluorescent compounds, as well as target the core structure to various regions of live cells. Such probes typically have high fluorescence quantum yields, especially in more apolar environments and certain ones can fluoresce in the far-red region of the visible spectrum. These dyes exhibit higher photostability as compared to other classes of dyes used conventionally in cell imaging, such as the BODIPY dyes.

Affinity Properties

Certain anthraquinones, anthrapyrazoles and benzophenoxazines are known to intercalate into DNA and interact with topoisomerase II, thereby inhibiting DNA replication and repair as well as RNA and protein synthesis. A large body of literature also exists with regard to their use in the treatment of cancer presumably due to the foregoing mechanism or other properties relating to intercalation. Due to their affinity for nucleic acids, these dyes have also found use with in vivo and in vitro methods where advantage is taken of their high level of specificity for nuclear staining. It has been unexpectedly found that the presence of various modifications on the core structures can alter the affinity of such molecules so that they can be used to identify organelles other than the nucleus. Thus, even though neither the modification group(s) or the dye have an affinity for the non-nuclear organelle, the modified dye exhibits this property. The use of various groups to alter the affinity of dyes towards a variety of different organelles has been described previously (Rosania et al., 2003 J Am Chem. Soc 125; 1130-1131 and Lee et al., 2003 Chem Commun 1852-1853) but these efforts involved styryl dyes that did not have any particular organelle affinity in and of themselves. In contrast, the present invention describes the alterations of dyes whose cores structures are known to have a nuclear affinity and redirecting them to a different organelle or suborganelle locus.

Typically, endoplasmic reticuli-targeting anthraquinone, anthrapyrazole and benzophenoxazine probes tend to be amphipathic, lipophilic cations with moderate-sized conjugated systems (This particular condition being met by the fluorophore core itself. Without wishing to be bound by theory, it appears that their moderately lipophilic character permits probe uptake by passive diffusion without nonspecific accumulation in biological membranes. The moderately amphipathic character favors uptake into the endoplasmic reticuli, perhaps owing to high concentrations of zwitterionic lipid head-groups in the organelle. Cationic amphiphilic anthraquinones, anthrapyrazoles and benzophenoxazines containing a basic moiety often accumulate in lysosomes or other acidic subcellular compartments. This lysosomotropism is thought to be due to the protonation of the dye within acidic organelles leading to the formation of a membrane-impermeable form. Highly lipophilic dyes show a greater propensity to accumulate in lysosomes than those with a lower lipophilicity. Selective mitochondrial accumulation involves electric potential, ion-trapping, and complex formation with cardiolipin. The basic mechanism for accumulation of mitochondrial probes relies upon their chemical structure, consisting of highly conjugated moieties that extensively delocalize a positive charge, thus allowing electrophoretic uptake toward the negatively charged matrix phase of the polarized inner mitochondrial membrane. However, although lipophilic cations are regarded as the most common mitochondriotropic dyes, electrically neutral and even potentially anionic dyes may accumulate in the mitochondria. Physicochemical features of probes which favor nucleic acid binding include cationic character and a planar aromatic system above a minimum size (This particular condition being met by the fluorophore core itself. Features which reduce accumulation in non-nuclear sites include high base strength and hydrophilicity of the cation.

While general guidelines for creating organelle-targeting anthraquinone, anthrapyrazole and benzophenoxazine probes can be provided, the basis of the selectivity of specific fluorochromes for various subcellular organelles, regions or domains in live cells is sometimes elusive. To clarify this, interactions of living cells with series of different anthraquinone, anthrapyrazole or benzophenoxazine molecules, having systematically varied physicochemical properties, should be analyzed experimentally and numerically using approaches such as quantitative structure activity relationship analysis (QSAR) and Fick-Nernst-Planck analysis. Typically, a single cell line or a panel of cell lines is incubated region or domain targeting functional groups may be covalently affixed to the anthraquinone, anthrapyrazole or benzophenoxazine core. Typically, either one or two such functional groups are affixed to the core structure, though in certain circumstances as many as four such groups can potentially be affixed to the fluorophore core. These are non-limiting examples of targeting groups that may find use with the present invention by being conjugated to an anthraquinone, anthrapyrazole or benzophenoxazine.

TABLE 1

Examples of functional groups (moieties) useful for generating fluorescent anthraquinone, anthrapyrazole and benzophenoxazine conjugates that are applicable to live cell imaging.

| Functional group (Moiety) | Subcellular target |
|---|---|
| γ-aminobutyryl atractyloside | ADP/ATP carrier in membranes |
| β-glucosamine | Lysosomes |
| alkyl amines, alkyl amine N-oxides, aliphatic amines, aliphatic amine N-oxides | Nucleus |
| brefeldin A | Endoplasmic Reticulum |
| cadaverine | Lysosome |
| ceramide | Golgi Body |
| cerebroside | Plasma membranes |
| colcemid or colchicine | Microtubule network |
| cycloheptaamylose | Cell surfaces |
| erythromycin | Bacterial ribosomes |
| galactoside | Bacterial membrane vesicles. |
| galactosyl, glycosyl or lactosyl ceramide | Endosome/Lysosome |
| ganglioside | Golgi Body |
| glibenclamide | Mitochondria |
| Guanidine, biguanidine | Mitochondria |
| glutathione | Microsomes |
| isocolchicine | Microtubule network |
| Mitochondrial localization sequence (MLS) peptides (e.g. MLSLRQSIRFFKGC, MSVLTPLLLRGLTGSARRLPVPRAKIHSL) | Mitochondria |
| mycolactone | Cytoplasm |
| N-(Acyl)-Sphingosines | Golgi Body |
| N-ε-D, L-lysine | cholesterol-free domains in membranes |
| N-acylcholines | Cholinergic receptors in membranes |
| norhexestrol and hexestrol | Estrogen-binding proteins in membranes |
| nystatin | Membranes |
| paclitaxel | Microtubule network |
| pentane | Lysosomes |
| Phallacidin or phalloidin | Microfilament network |
| phosphatidylcholine or phosphatidylethanolamine | Membranes |
| polymyxin | Lipopolysaccharide and lipid A in bacteria |
| propranolol | Calcium-magnesium-ATPase in membranes |
| protamine | Mucopolysaccharide layers |
| ryanodine | Nuclear envelope |
| spermidine and spermine | Endosomes |
| steroid (e.g. cholesterol, coprostanol) | Lipid rafts |
| taurine | Basolateral membrane |
| thapsigargin | Nuclear envelope |
| trimethylammonia | Basolateral organic cation transporters of proximal tubule |
| vinblastine | Mitochondria | with different concentrations (typically 1-100 μM) of the potential organelle-targeting compounds and subcellular distribution is monitored by wide-field fluorescence microscopy. Combinatorial synthesis of panels of anthraquinone, anthrapyrazole or benzophenoxazine derivatives may be subjected to cell-based screening in order to identify lead compounds with desired localization properties.

Dyes Conjugated to Organelle Specific Moieties

In another embodiment of the present invention, we have found that the combination of nuclear dye with a moiety that has an affinity for a locus other than the nucleus can result in a conjugate that retains the ability to target the non-nuclear organelle and endowing it with the spectral properties of the dye. It has been found that a variety of subcellular organelle, Conjugation may take place with an organelle specific moiety in combination with an anthraquinone, anthrapyrazole or benzophenoxazine that in unconjugated form accumulates in the nucleus, or contrariwise, the dye may be a modified version, as described above, such that both the organelle specific moiety and the dye have an affinity for the same organelle, thereby potentially increasing the specificity of the conjugate to the organelle of interest.

Inclusion of Spacer Groups for Substituted Anthraquinone, Anthrapyrazole and Benzophenoxazine Probes:

In some cases it is advisable to employ an intervening spacer group (a.k.a. linker region) in order to ensure biological targeting of the anthraquinone, anthrapyrazole or benzophenoxazine probe. The spacer group minimizes steric interference between the organelle-targeting group and the fluorophore. For example, a hexanoic spacer group may be used between the anthraquinone moiety and the organelle-targeting functional group. This spacer may be created using a compound such as 6-amino hexanoic acid. In other instances a methyl-, ethyl-, propyl-, butyl-, pentyl-, hexyl-, heptyl, or octyl-methylene spacer may be required. Piperazine, 1-(2-aminoethyl) piperazine, ε-aminohexanoyl and ε-aminocaproyl are also suitable spacer groups in some instances. The length of the spacer group may vary from a single methylene residue to a long polymer, employing such spacers as poly(ethylene glycol), for example. Aliphatic or hetero-aliphatic spacer groups may be employed, as can peptide-, oligonucleotide-, or peptide nucleic acid-based spacer groups.

Probes for lipid microdomains, or rafts that have formed as a result of specific lipid-lipid or lipid-protein interactions in the cell membrane, are important tools for analysis of the regulation of signal transduction, cellular transport, and lipid sorting. A specific example of domain-targeting anthraquinone, anthrapyrazole or benzophenoxazine probes requiring spacer groups are cholesteryl esters, in which a fluorophore is esterified to the $C_3$-hydroxy group of the sterol. Without wishing to be bound by theory, it appears that bending or looping of a flexible acyl linker region is required in order for such probes to effectively intercalate into lipid rafts in the plasma membrane. Alternatively, when creating free cholesterol-dye conjugates, different linkers may be used to couple the fluorophore to the sterol's aliphatic side chain. The cholesterol ester derivatives require much longer linkers (~$C_{10}$-$C_{12}$ alkyl chains) than the free cholesterol derivatives (~$C_1$-$C_3$ alkyl chains) to achieve biologically active compounds. The structure of the linker region used to ligate the anthraquinone, anthrapyrazole or benzophenoxazine moiety to the $C_3$-hydroxyl or aliphatic side chain of the sterol, is an important determinant of the ability of the probe to partition into liquid-ordered versus liquid-disordered membrane domains.

Formulations and Compositions

Compositions according to the invention comprise a compound of the invention and are intended to include any and all solvents, dispersion media, coatings, isotonic and absorption delaying agents, and the like, compatible with the application. Except insofar as any conventional media or agent is compatible with the active compound, such media can be used in the compositions of the invention. Supplementary active compounds can also be incorporated into the compositions.

For example, when a composition of the invention is applied to cells or tissues, it is formulated to be compatible with the intended route of entry into the cells or tissues. For example, isotonic saline solutions, mildly hypertonic saline solutions, phosphate-buffered saline, cell culture media, isotonic sucrose solutions, or mildly hypertonic sucrose solutions may serve as the vehicle for delivery of the compound to the cells. Polyethylene glycols, glycerin, dimethylsulfoxide, dimethylformamide, propylene glycol, or other co-solvents may be included to facilitate solubilization of the compound. Antibacterial agents, such as benzyl alcohol or methyl parabens; antioxidants, such as ascorbic acid or sodium bisulfite; chelating agents, such as ethylenediaminetetraacetic acid (EDTA) or cyclodextrin; buffers, such as acetates, phosphates or citrates; agents for adjusting tonicity, such as sodium chloride or sucrose; and agents that adjust the pH value of the delivery vehicle, such as sodium hydroxide and hydrochloric acid may be incorporated in the formulation of the compound.

Compositions of the said invention may include certain anions and cations (e.g. alkyl metal chlorides) to facilitate penetration of the compound thru cell membranes. Non-limiting examples of anions include barbital, bicarbonate, borate, chloride, oxylate or EDTA. Not all anions have been found suitable for promoting penetration of cell membranes. Non-limiting examples of cations include sodium (as in sodium chloride), potassium (as in potassium chloride), trishydroxymethylamino methane (TRIS), tris[hydroxymethyl]-aminomethane-hydrochloric acid (TRIS-HCL), or triethanolamine (TEA).

Overall Advantages of Substituted Anthraquinone, Anthrapyrazole and Benzophenoxazine Probes:

The perceived brightness of a fluorochrome is determined by several intrinsic factors, including the fluorophore's molar extinction coefficient and quantum yield, as well as extrinsic factors such as the optical properties of the imaging setup (illumination wavelength and intensity, spectra of filters and dichroic mirrors), and the camera's sensitivity to the emission spectrum. A common misperception in the fluorescent probe industry is that fluorophores with the highest molar extinction coefficient and quantum yield provide superior performance. However, other factors should be considered as well when assessing overall performance of a fluorochrome in particular applications. For instance, despite relatively low quantum yield (QY=0.004) and modest molar extinction coefficient (ε=45,000), anthraquinone-based fluorophores are actually superior to BODIPY and cyanine-based ones in live cell imaging applications when these other factors are taken into consideration. The dyes are highly resistant to photo-bleaching, display minimal concentration quenching upon sequestering in organelles, and possess excitation/emission profiles that are ideal for multiplexing with most commonly used fluorochromes. Far-red emitting anthraquinones can be excited by a wide range of convenient laser light wavelengths (488, 514, 568, 633 or 647 nm). The dye family's emission spectrum extends from 670 nm into the low infra-red region, providing minimal overlap with the emission spectra from UV and visible range dyes and photoproteins.

For example, GFP and the far red-emitting anthraquinone derivatives can be co-excited at 488 nm, generating clear spectral separation of the emission signals in live cells, and thus allowing live cell single-pass laser-scanning. This is an important factor in increasing throughput rate and permits live cell assays to track agonist/antagonist responses over time frames of minutes. In flow cytometry and laser scanning applications, far red-emitting substituted anthraquinones obviate the need for spectral compensation when used in conjunction with fluorescein or GFP-labeled probes.

Two-photon absorption can be used, in which two long wavelength photons, absorbed by the fluorochrome, promote it to an excited state that then emits a single photon of higher energy. This is an approach suitable for exciting intracellular or tissue samples at a wavelength that is more transparent to these media. The dependence of two-photon absorption on the intensity of the laser beam allows for high spatial selectivity by focusing the laser beam on the target cell and thus preventing any damage to adjacent cells. Relatively few dyes are suitable for practical experiments using two-photon excitation because most do not absorb two long wavelength photons efficiently, i.e., they have poor two-photon cross-sections. One issue with two-photon excitation experiments is that the emitted light is of a short wavelength compared to the excitation source, and this might not be in a convenient region to permeate out of cells of other tissues, and for detection. With the cited far-red emitting anthraquinones, however, two-photon excitation is possible beyond 1000 nm wavelengths. Also important relative to multi-color labeling applications is that the far red-emitting anthraquinones are two-photon dark for the Titanium-Sapphire laser range 700-850 nm wavelengths.

The far red-emitting fluorochromes, described herein, emit at wavelengths to which blood and tissue are relatively transparent. Since the fluorochromes will not absorb wavelengths that tissues absorb strongly, and do not have emission wavelengths that will be absorbed significantly by tissues, their signals are readily transmitted through tissues, allowing imaging of components within complex biological fluids, such as blood, as well as deeply within tissues, organs or even certain organisms.

Substituted Anthraquinone and Benzophenoxazine Probes for Multi-Parametric Analyses:

The invention relates to substituted anthraquinone and benzophenoxazine dyes suitable for use with a variety of imaging and detection instrumentation including, but not limited to, fluorimeters, spectrofluorimeters, fluorometric plate readers, flow cytometers, microarray readers, fluorescence microscopes, fluorescence imaging systems, fluorescence microvolume cell analysis instruments, robotic fluorescent colony pickers, capillary electrophoresis systems with fluorescence detectors, fluorescence-based lab-on-a chip devices or fluorescence-based microfluidic devices. Macroscopic, microscopic or nanoscopic imaging may be performed in conjunction with the compounds of the invention The described dyes may be applied to a wide variety of fluorescence-based detection and quantification strategies including, but not limited to, fluorescence lifetime imaging (FLI), fluorescence lifetime imaging microscopy (FLIM), Fluorescence lifetime imaging endoscopy (FLIE), fluorescence loss in photobleaching (FLIP), chromophore-assisted light inactivation (CALI), fluorescence resonance energy transfer (FRET), fluorescence recovery after photobleaching (FRAP), fluorescence recovery after photo-activation (FRAPa), fluorescence correlation spectroscopy (FCS), polarized fluorescence recovery after photobleaching (PFRAP), single-molecule fluorescence energy transfer (smFRET), fluorescence imaging with one nanometer accuracy (FIONA), single-molecule high-resolution colocalization (SHREC), super high resolution imaging with photobleaching (SHRIMP), total internal reflection fluorescence (TIRF), defocused orientation position imaging (DOPI), fluorescence photoactivation localization microscopy (FPALM), biplane FPALM (BP-FPALM), two-photon laser scanning fluorescence microscopy (2PLSM), three-photon laser scanning fluorescence microscopy (3PLSM), extended field laser confocal microscopy (EFLCM), time-gated luminescence (TGL), stimulated emission depletion (STED), large-area multiphoton laser scanning microscopy (LMLSM), three-dimensional structured illumination microscopy (3D-SIM), simultaneous spatial and temporal focusing (SSTF), spatially modulated illumination (SMI), Femtosecond Kerr-gated wide-field fluorescence microscopy, structured illumination wide-field fluorescence microscopy (SIWFFM), higher harmonic generation microscopy (HHGM), stochastic optical reconstruction microscopy (STORM), variable-angle epifluorescence microscopy (VAEM), multidirectional selective plane illumination microscopy (mSPIM), variable-angle total internal reflection fluorescence microscopy (VA-TIRFM), fluorescence microphotolysis (CFM), coherent anti-Stokes Raman scattering (CARS), fluorescence ratio imaging microscopy, time-correlated single-photon counting (TCSPC), dynamic speckle illumination (DSI), standing wave total internal reflection fluorescence (SW-TIRF), reversible saturable/switchable optical transitions (RESOLFT), confocal and multiphoton laser scanning microscopy (CLSM), 4Pi microscopy, I(5) microscopy, and spectrally resolved fluorescence lifetime imaging microscopy (SFLIM).

Examples of fluorochromes and fluorescent proteins that the new red and/or far-red emitting probes are spectrally compatible with in terms of multi-color imaging applications are summarized in table 2. Note that some of the fluorochromes listed in the table are cell-impermeable, but are often affixed to antibodies for cell surface-based multi-parametric live cell analysis.

TABLE 2

Commonly used fluorochromes in live cell imaging.

| Fluorochrome | Excitation maximum (nm) | Emission maximum (nm) |
| --- | --- | --- |
| 5-Hydroxytryptamine (HAT) | 370-415 | 530 |
| Acridine orange | 500 | 526 |
| Acridine yellow | 470 | 550 |
| Alexa Fluor 532 | 530 | 555 |
| Alexa Fluor 546 | 554 | 570 |
| Alexafluor 488 | 494 | 519 |
| Blue Fluorescent Proteins (e.g. EBFP, EBFP2, Azurite, mKalama) | 383 | 445 |
| BODIPY-FL | 505 | 513 |
| Cascade Blue | 377 | 420 |
| Coelenterazine | 429 | 466 |
| Coumarin | 384 | 470 |
| Cyan Fluorescent Proteins (e.g. ECFP, Cerulean, CyPet, mCFP, AmCyan1, Midoriishi Cyan) | 435 | 475 |
| Cyanine 2 | 492 | 510 |
| Cyanine 3 | 550 | 570 |
| Cyanine 5 | 650 | 670 |
| Dansyl | 340 | 520 |
| DAPI | 358 | 461 |
| Erythrosin | 529 | 554 |
| Far-red Fluorescent Proteins (e.g. mPlum, AQ143) | 590 | 649 |
| FLUO 3 | 506 | 526 |
| Fluorescein | 495 | 525 |
| FURA 2 (ratiometric) | 362, 335 | 512, 505 |
| Green Fluorescent Proteins (e.g. EGFP, Emerald, aceGFP, TurboGFP, Azami Green, ZsGreen) | 490 | 509 |
| Hoechst 33258 or Hoechst 33342 | 352 | 461 |

TABLE 2-continued

Commonly used fluorochromes in live cell imaging.

| Fluorochrome | Excitation maximum (nm) | Emission maximum (nm) |
|---|---|---|
| INDO 1 (ratiometric) | 349, 331 | 482, 398 |
| JC-1 (monomer, J-aggregate) | 510, 585 | 527, 590 |
| Lucifer Yellow | 488 | 550 |
| Nile Red | 485 | 525 |
| Oregon Green 488 | 493 | 520 |
| Propidium iodide | 305, 536 | 617 |
| QUIN 2 (ratiometric) | 354, 332 | 510, 505 |
| Red fluorescent proteins (e.g. mCherry, tdTomato, mStrawberry, J-Red, DsRed, Kusabira Orange, AsRed2, mRFP1, HcRed1, mRaspberry) | 570 | 590 |
| Rhodamine 110 | 496 | 520 |
| Rhodamine 123 | 505 | 534 |
| Rhodamine 6G | 525 | 555 |
| Rhodamine B | 540 | 625 |
| R-Phycoerythrin | 488 | 575 |
| R-Phycoerythrin-Texas Red | 480-565 | 615 |
| SNARF | 480 | 600/650 |
| Texas Red | 596 | 620 |
| UV-excitable Green Fluorescent Proteins (T-Sapphire) | 399 | 511 |
| Yellow fluorescent proteins (e.g. EYFP, Citrine, Venus, YPet, Topaz, PhiYFP, ZsYellow1, mBanana). | 516 | 530 |

Although linear unmixing systems should provide the ability to distinguish among large numbers of different fluorophores with partially overlapping spectra, it is possible, even with a simpler optical setup in wide-field microscopy, to clearly distinguish among four different fluorescent proteins along, with one of the substituted far red-emitting anthraquinone or benzophenoxazine dyes of the present invention. For instance, using appropriate filter sets, one may simultaneously image cyan, yellow, orange and red fluorescent proteins (Cerulean or CyPet, any YFP, mOrange or mKO and mCherry) along with any of the far-red emitting dye derivatives described in this application, with minimal spectral cross-talk. One possible filter set combination appropriate for performing such an experiment is summarized in Table 3.

TABLE 3

Possible filter set combination for 5-parameter imaging with various fluorescent proteins and an anthraquinone dye.

| Fluorochrome | Excitation filter (nm) | Emission filter (nm) |
|---|---|---|
| Cerulean or CyPet | 425/20 | 480/40 |
| mCitrine or YPet | 495/10 | 525/20 |
| mOrange or mKO | 545/20 | 575/25 |
| mCherry | 585/20 | 624/40 |
| Anthraquinone derivative | 628/40 | 695LP, 715LP or 780LP |

The described far red-emitting fluorochromes may also be used in conjunction with antibodies conjugated with various fluorochromes, such as fluorescein, R-phycoerythrin, and R-phycoerythrin-Texas Red, using a flow cytometer equipped with a single argon laser emitting 488-nm laser source. Despite this sub-optimal excitation wavelength, which results in more than a 20-fold reduction in peak fluorescence, the anthraquinones are concentrated and sequestered in organelles and sufficiently bright for the analysis. Suitable emission filter settings for performing this type of analysis are summarized in table 4. Fluorescence of the antigen staining would likely be collected in logarithmic mode and the anthraquinone staining in linear mode. No cell fixation step is required and no spectral compensation from either the emission spectra of R-phycoerythrin or R-phycoerythrin/Texas Red tandem conjugate is needed, because the particular anthraquinone derivatives emit in the far-red region of the spectrum.

TABLE 4

Possible emission filter set combination for 4-parameter flow cytometry measurements using various fluorescently-labeled antibodies and an anthraquinone dye.

| Fluorochrome | Emission filter (nm) |
|---|---|
| Fluorescein | 530/30 BP |
| R-Phycoerythrin | 585/42 BP |
| R-Phycoerythrin-Texas Red | 620/20 BP |
| Anthraquinone derivative | 675 LP |

Other anthraquinones, according to the invention, possess spectral properties that are analogous to mCherry, Texas Red or Nile Red dyes. These may be extensively multiplexed as well, for example substituting for mCherry in table 3 or R-phycoerythrin-Texas Red in table 4 and allowing addition of a far-red emitting dye, such as Draq-5, Alexafluor 660 conjugate, Alexafluor 680 conjugate, TOPRO-3, Spectrum FarRed or another far red-emitting anthraquinione or benzophenoxazine dye, as delineated by the present invention.

Detection and Isolation of Subcellular Organelles:

The preparation of samples for biochemical analysis of protein activity frequently requires cell lysis, followed by fractionation and purification of subcellular organelles. For instance, some apoptosis assays rely upon the isolation of cytosolic and mitochondrial cell fractions in order to monitor the release of cytochrome c from the mitochondria. In other assays, a nuclear fraction must be isolated in order to monitor translocation of steroid hormone receptors from the cytoplasm to the nucleus. In such assays, rapid isolation of the targeted organelle is crucial, especially when monitoring early biochemical events arising from the activation of cells. While many of these traditional biochemical assays are increasingly being displaced by imaging-based cell assays, detailed analysis of proteins at the molecular level, especially with respect to post-translational modifications and proteinligand interactions, is particularly important to fields, such as proteomics and systems biology. Common methods for subcellular fractionation include density-gradient centrifugation, free flow electrophoresis, immuno-magnetic separation and field flow fractionation in microfabricated devices (Lab-on-chips). Once isolated, the desired fractions are typically identified based upon enrichment and specific activity of surrogate enzymes known to be localized to that organelle.

The various anthraquinone-, phenoxazine-, anthrapyrazole- and benzophenoxazine-based fluorochromes, alone or in combination with other fluorochromes and/or fluorescent proteins, provide a convenient tool for highlighting multiple organelles during their purification for enzyme assays, as well as, proteomics and systems biology applications, wherein multiple analyte profiling is subsequently performed. For instance, cells may be incubated with the anthraquinone in combination with Hoechst 33258 and JC-1 in order to label the lysosomal, nuclear and mitochondrial fractions, respectively. Cells are lysed and then subcellular fractions isolated using, for example, an 18 cm long, 1 mm wide, 50 µm deep microfabricated field flow fractionation device mounted to an inverted fluorescence microscope that is equipped with a digital camera. Roughly two volts is applied across the chamber and the lysed cells are introduced into the chamber of the device. Initially, the various organelles are distributed evenly throughout the chamber, as demonstrated by diffuse fluorescence through out, but as they flow through the chamber, the pH gradient develops and focusing of the various organelles occurs as demonstrated by the appearance of blue-red- and far red-emitting zones that represent nuclei, mitochondria and lysosomes, respectively. A fourth green-emitting zone is also usually observable, representing mitochondria stained with JC-1 monomer—(as opposed to J-aggregate), representing those mitochondria that have lost their transmembrane potential. Typically, 5-10 minutes is required in order to reach a steady state separation. The four zones may then be collected using a flow splitter at the end of the isoelectric focusing chamber, for further refinement of the separation process or for subsequent analysis by conventional enzymology, proteomics or systems biology approaches.

Other Applications

The novel dyes and compositions of the present invention can also be used in other applications. For instance, numerous molecules, such as DDAO-phosphate (7-hydroxy-9H-(1,3-dichloro-9,9-dimethylacridin-2-one phosphate) and difluorinated methylumbelliferyl phosphate (DiFMUP), are known to undergo changes in optical characteristics when one or more phosphate groups are removed. This removal and change serves as a basis for numerous phosphatase assays that have been described in the literature. Accordingly, in the present invention, the anthraquinones, the phenoxazines, the anthrapyrazoles and the benzophenoxazines may be synthesized with a phosphate moiety in an appropriate location of the molecule, thus making it useful and applicable in phosphatase activity measurement. Cell permeability may be facilitated through creation of phosphate esters, with regeneration of the phosphomonoester occurring after cell uptake, upon intracellular cleavage by endogenous esterases. Organelle-targeting of the anthraquinone phosphate ester, according to the present invention, permits localization of the substrate to regions of the cell where particular phosphatases or phosphatase family members reside. For example, lysosomal targeting is useful for measuring acid phosphatase activity, while plasma membrane targeting affords some measure of selectivity for protein tyrosine phosphatase 1B (PTP1B), which is known to negatively regulate EGF-induced signaling in several cell types by dephosphorylating the epidermal growth factor receptor (EGFR). Similar strategies can be employed to detact, localize or quantify β-glucuronidases, β-galactosidases, esterases, lipases, chitinase/N-acetylglucosaminidases or sulfatases, as nonlimiting examples.

In another embodiment of the present invention, the fluorescent capabilities of the anthraquinones, anthrapyrazoles and benzophenoxazines may also be used as labeling reagents where the presence of a reactive group on such molecules may allow their attachment to various targets. Such targets can include but not be limited to proteins and nucleic acids. These labeling reagents may also be part of oligomeric or polymeric complexes that may be used to attach multiple fluorescent molecules to a single site on targets such as proteins or nucleic acids, thereby providing tagged molecules with very high signal generating capability.

Reagent Kits:

Commercial kits are valuable because they eliminate the need for individual laboratories to optimize procedures, saving both time and resources. They also allow better cross-comparison of results generated from different laboratories. The present invention additionally provides reagent kits, i.e., reagent combinations or means, comprising all of the essential elements required to conduct a desired assay method. The reagent system is presented in a commercially packaged form, as a composition or admixture where the compatibility of the reagents will allow, in a test kit, i.e., a packaged combination of one or more containers, devices or the like holding the necessary reagents, and usually written instructions for the performance of the assays. Reagent systems of the present invention include all configurations and compositions for performing the various labeling and staining formats described herein.

The reagent system will generally comprise (1.) one or more substituted anthraquinone, anthrapyrazole or benzophenoxazine fluorochrome designed to target specific subcellular organelles, cell regions or cell domains. (2.) Instructions for usage of the included reagents. Generic instruction, as well as specific instructions for the use of the reagents on particular instruments, such as a wide-field microscope, confocal microscope, flow cytometer or microplate-based detection platform may be provided. Recommendations regarding filter sets and/or illumination sources for optimal performance of the reagents for a particular application may be provided.

A test kit form of the system for lysosomal labeling, for example, can contain one or more substituted anthraquinone, phenoxazines, anthrapyrazole or benzophenoxazine fluorochromes that localize to the lysosome, and additional ancillary chemicals, such as dilution buffer, live-cell DNA stain, live-cell mitochondrial stain and/or an antibody, a lectin, a $Ca^{2+}$-dependent, phospholipid binding protein (such as Annexin V), or other reporter labeled with a fluorophore. In some instances one or more fluorochrome may be combined within a single container for easier use. In some instances, calibrants are included, such as microsphere or bead standards of known fluorescent output.

Therapeutic Activity

The anthracycline doxorubicin, a DNA-targeting drug, is among the most versatile chemotherapeutic agents currently in clinical use. However, the proven clinical utility of doxorubicin has been tempered by dose-limiting cardiotoxicity, and this has prompted a search for analogs with comparable therapeutic efficacy, yet lacking the characteristic cardiotoxicity. Members of the anthracenedione class of compounds were identified as good drug candidates designed to satisfy these criteria. The anthracenediones, most notably mitoxantrone (Novatrone™) are simplified anthracycline analogues, which retain the planar ring structure characteristic of anthracyclines, permitting intercalation between base pairs of DNA.

Mitoxantrone (MTX) is an antineoplastic agent used in the treatment of certain types of cancer, mostly metastatic breast cancer, acute myeloid leukemia, and non-Hodgkin's lymphoma, as well as secondary progressive multiple sclerosis (MS). Without wishing to be bound by theory, it is believed that MTX displays cytotoxic activity when it poisons topoisomerase II by stabilizing the ternary, DNA-intercalator-Topo complex in such a way that the enzymatic process cannot continue forward or backward. The ternary complex is detected by the cell as a damaged portion, which triggers a series of events; one of the more important ones involving p53 protein, which induces cell apoptosis. Despite an improved clinical tolerability of MTX chemotherapy, it still exerts a range of toxic side-effects including myelosuppression and cardiotoxicity. One unfortunate side effect of the drug is that it undergoes redox cycling, giving rise to an accumulation of free radical species at the cardiac level.

MTX can be found as four intracellular species: nuclear MTX bound to DNA, MTX oxidative metabolite in endoplasmic reticulum, cytosolic MTX, and MTX in low polarity membranes. Only about 50% of the drug is actually associated with the nucleus and we believe it is the portion of the drug localized in the cytosolic compartments that leads to the generation of ROS, leading to cardiotoxicity. Drug metabolism and compartmentalization are key aspects of cell chemosensitization. Examples 25 and 26 demonstrate that the compounds described in this invention can have cytoxic or cytostatic activity in cancer cells. Better nuclear targeting of the carbocyclic anthraquinone core using compounds described in this invention will reduce cardiotoxicity and improve efficacy for this class of drugs. In general, improving the therapeutic profile of various drugs can be accomplished thru rational design that leads to better compartmentalization of the drug within the targeted region of the cell, and the compounds of this invention accomplish that goal. The fluorescence signature of the compounds is valuable in screening the compounds for their localization properties. While the principle is illustrated with DNA targeting antineoplastic agents, the same principle can be applied to other subcellular compartments, such as, for example, improving efficacy of mitochondriotoxic drugs. The potency and selectivity of drugs may be improved thru their selective targeting to different subcellular locations.

The following examples are offered by way of illustration and not by way of limitation to the present invention.

DESCRIPTION OF THE PREFERRED EMBODIMENTS

Table 5 summarizes the various examples of organelle-targeting fluorochromes according to the present invention. Immediately following Table 5 is Table 6 which provides a cross-reference among the compounds, intermediaries used in synthesis, examples and targetted organelle(s).

TABLE 5

Examples of Organelle-Targeting Fluorochromes

| STRUCTURE | DESIGNATION | CHEMICAL NAME | PRIMARY TARGET |
| --- | --- | --- | --- |
| 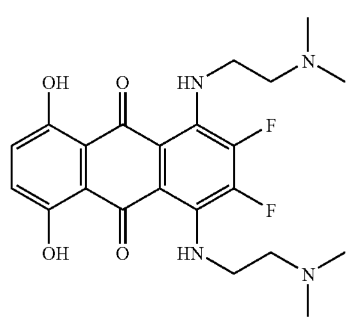 [SMILES: CN(C)CCNc1c(F)c(F)c(NCCN(C)C)c2c1C(=O)c1c(O)ccc(O)c1C2=O] | Compound 1 | 1,4-bis(2-(dimethylamino) ethylamino)-2,3-difluoro-5,8-dihydroxyanthracene-9,10-dione | Lysosome |
| 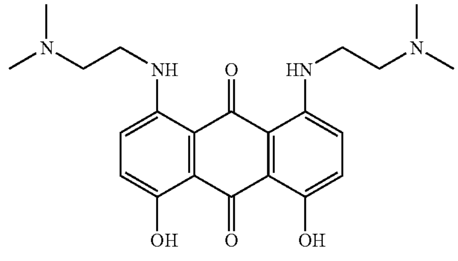 | Compound 7 | 1,8-bis(2-(dimethylamino) ethylamino)-4,5 dihydroxy anthracene-9,10-dione | Lysosome |

TABLE 5-continued

Examples of Organelle-Targeting Fluorochromes

| STRUCTURE | DESIGNATION | CHEMICAL NAME | PRIMARY TARGET |
|---|---|---|---|
| 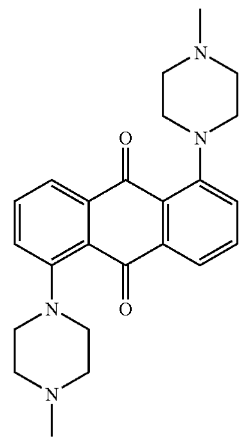 [SMILES: CN1CCN(c2cccc3c2C(=O)c2cccc(N4CCN(C)CC4)c2C3=O)CC1] | Compound 11 | 1,5-bis(4-methyl piperazin-1yl)anthracene-9,10-dione | Nucleus |
| 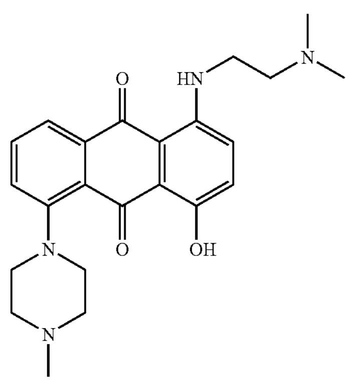 [SMILES: CN(C)CCNc1ccc(O)c2c1C(=O)c1cccc(N3CCN(C)CC3)c1C2=O] | Compound 19. | 1-(2-dimethylamino) ethylamino)-4-hydroxy-5-(4-methylpiperazin-1-yl)anthracene-9,10-dione | Nucleus |
| 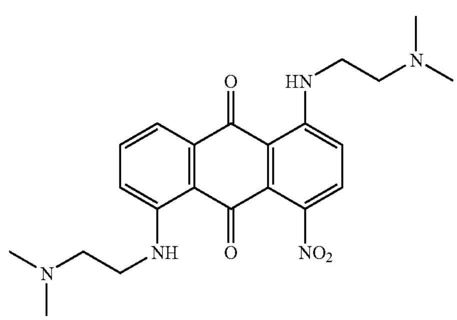 | Compound 15 | 1,5-bis(2-(dimethylamino) ethylamino)-4-nitroanthracene-9,10-dione | Nucleus |
| 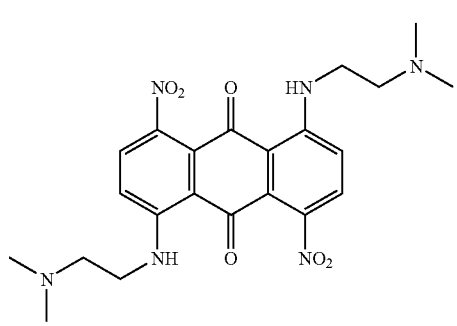 | Compound 16 | 1,5-bis(2-(dimethylamino) ethylamino)-4,8-dinitroanthracene-9,10-dione | Nucleus |

TABLE 5-continued

Examples of Organelle-Targeting Fluorochromes

| STRUCTURE | DESIGNATION | CHEMICAL NAME | PRIMARY TARGET |
|---|---|---|---|
| 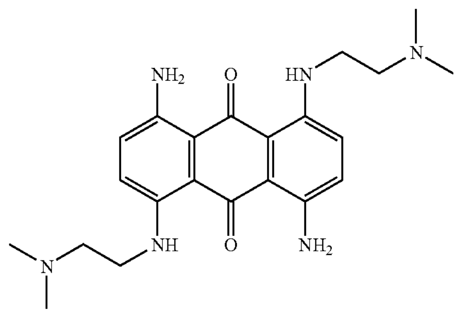 | Compound 20 | 1,5-diamino-4,8-bis(2-(dimethylamino)ethyl amino)anthracene-9,10-dione | Nucleus |
| 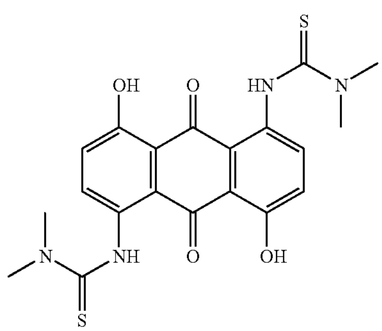 | Compound 8 | 1,1'-(dihydroxy-9,10-dioxo-9,10-dihydro anthracene-1,5-diyl)bis(3,3-dimethyl thiourea) | Cytosol + Mitochondria |
| 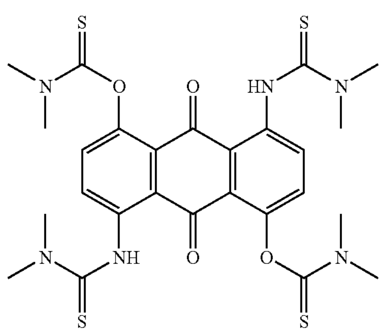 | Compound 10 | O,O'-4,8-bis(3,3-dimethylthioureido)-9,10-dioxo-9,10-dihydroanthracene-1,5-diyl bis(dimethyl carbamothioate) | Cytosol + Mitochondria |
| 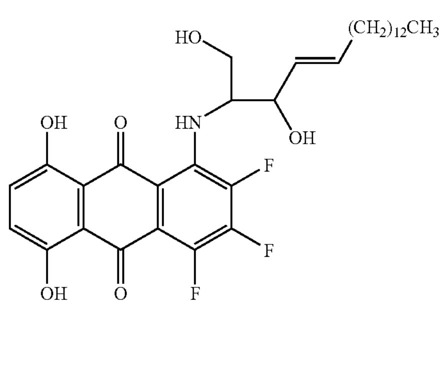 | Compound 2 | 1-(1,3-dihydroxy octadec-4-en-2-yl amino)-2,3,4-trifluoro-5,8-dihydroxy anthracene-9,10-dione | Golgi |

TABLE 5-continued

Examples of Organelle-Targeting Fluorochromes

| STRUCTURE | DESIGNATION | CHEMICAL NAME | PRIMARY TARGET |
|---|---|---|---|
| 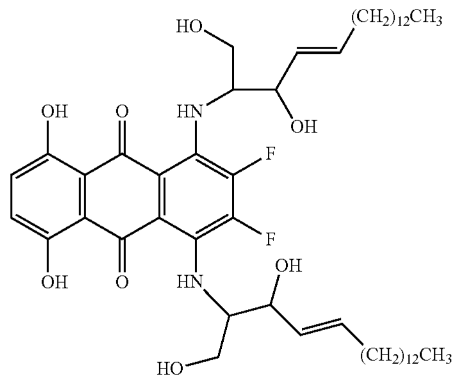 | Compound 3 | (1,4-(1,3-dihydroxy octadec-4-en-2-yl amino))-2,3-difluoro-5,8-dihydroxy anthracene-9,10-dione | Golgi |
| 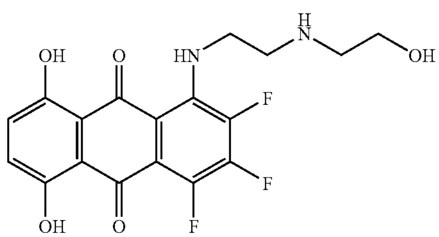 [SMILES: O=C1c2c(O)ccc(O)c2C(=O)c2c(NCCNCCO)c(F)c(F)c(F)c21] | Compound 4 | 1,2,3-trifluoro-5,8-dihydroxy-4-(2-(2-hydroxyethylamino)ethyl-amino)anthreacene-9,10-dione | Total Cell Stain |
| 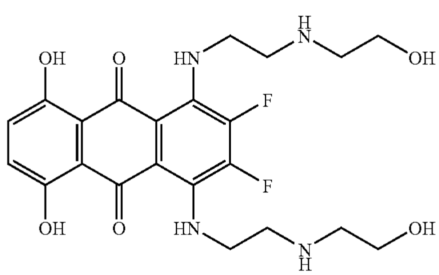 [SMILES: O=C1c2c(O)ccc(O)c2C(=O)c2c(NCCNCCO)c(F)c(F)c(NCCNCCO)c21] | Compound 5 | 2,3-difluoro-5,8-dihydroxy-1,4-bis(2-(2-hydroxyethylamino) ethylamino) anthreacene-9,10-dione | Total Cell Stain |
| 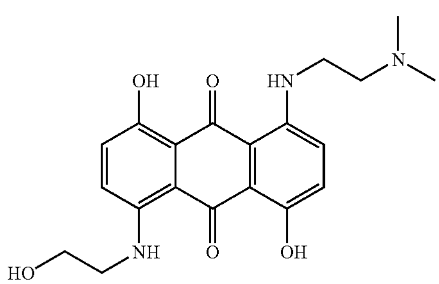 [SMILES: CN(C)CCNc1ccc(O)c2c1C(=O)c1c(O)ccc(NCCO)c1C2=O] | Compound 22 | 1-(2-(dimethylamino) ethylamino-4,8-dihydroxy-5-(2-hydroxy ethylamino)anthracene-9,10-dione | Total Cell Stain |
| 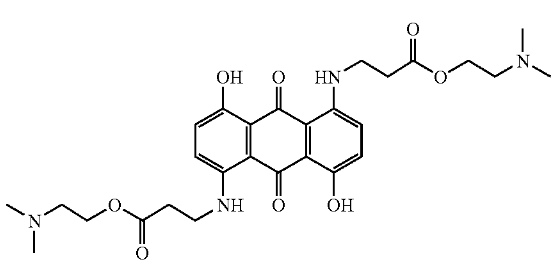 | Compound 12 | bis(2-dimethylamino) ethyl)3,3'-(4,8-dihydroxy-9,10-dioxo-9,10-dihydroanthracene-1,5-diyl) bis(azanediyl) dipropanoate | Total Cell Stain |

TABLE 5-continued

Examples of Organelle-Targeting Fluorochromes

| STRUCTURE | DESIGNATION | CHEMICAL NAME | PRIMARY TARGET |
|---|---|---|---|
| 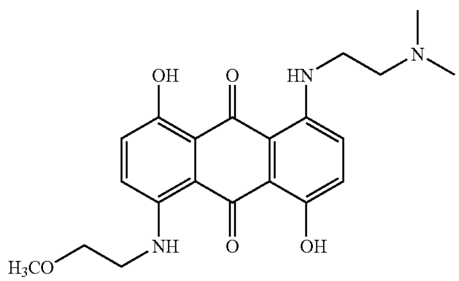 [SMILES: COCCNc1ccc(O)c2c1C(=O)c1c(O)ccc(NCCN(C)C)c1C2=O] | Compound 24 | 1-(2-(dimethylamino)ethylamino-4,8-dihydroxy-5-(2-methoxyethylamino)anthracene-9,10-dione | Total Cell Stain |
| | Compound 26 | 1,5-dihydroxy-4,8-bis(2-methoxyethylamino)anthracene-9,10-dione | Total Cell Stain |
| 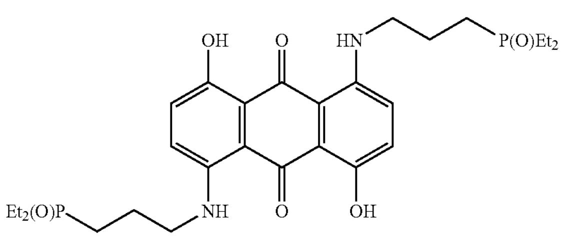 | Compound 13 | 1,5-bis(3-(diethylphosphoryl)propylamino)-4,8-dihydroxyanthracene-9,10-dione | Vesicle |
| 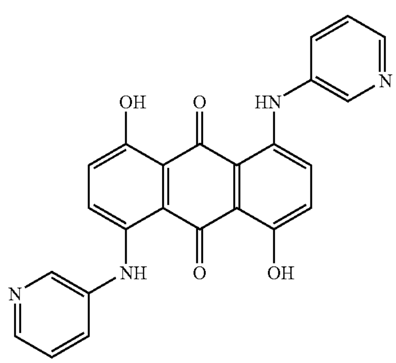 [SMILES: O=C1c2c(O)ccc(Nc3cccnc3)c2C(=O)c2c(O)ccc(Nc3cccnc3)c21] | Compound 28 | 1,5-dihydroxy-4,8-bis(pyridin-3-ylamino)anthracene-9,10-dione | Vesicle |
| | Compound 26 | 1,5-dihydroxy-4,8-bis(2-methoxyethylamino)anthracene-9,10-dione | Total Cell Stain |

TABLE 5-continued

Examples of Organelle-Targeting Fluorochromes

| STRUCTURE | DESIGNATION | CHEMICAL NAME | PRIMARY TARGET |
|---|---|---|---|
| (structure) | Compound 13 | 1,5-bis(3-(diethyl phosphoryl) propylamino)-4,8-dihydroxyanthracene-9,10-dione | Vesicle |
| (structure) | Compound 28 | 1,5-dihydroxy-4,8-bis(pyridin-3-ylamino) anthracene-9,10-dione | Vesicle |
| (structure) | Compound 26 | 1,5-dihydroxy-4,8-bis(2-methoxyethylamino)-anthracene-9,10-dione | Total Cell Stain |
| (structure) | Compound 13 | 1,5-bis(3-(diethyl phosphoryl) propylamino)-4,8-dihydroxyanthracene-9,10-dione | Vesicle |
| (structure) | Compound 28 | 1,5-dihydroxy-4,8-bis(pyridin-3-ylamino) anthracene-9,10-dione | Vesicle |

TABLE 5-continued

Examples of Organelle-Targeting Fluorochromes

| STRUCTURE | DESIGNATION | CHEMICAL NAME | PRIMARY TARGET |
|---|---|---|---|
| 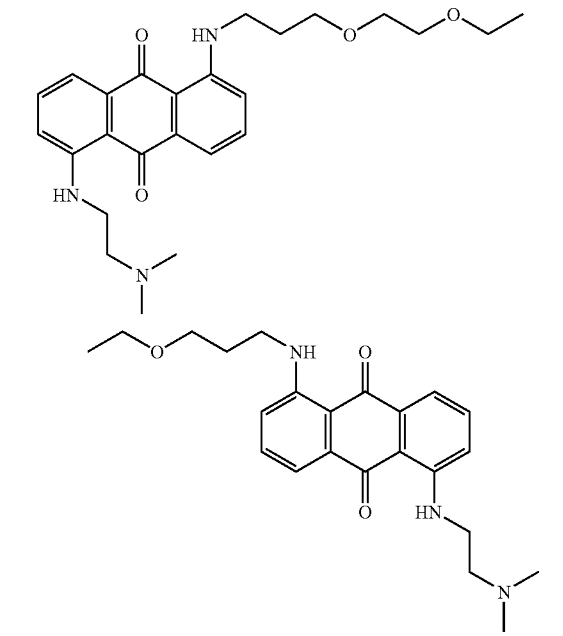 | Compound 29 | 5,5'-(3,3'-oxy bis(ethane-2,2-diyl)bis(oxy))bis-(propane-3,1-diyl)bis(1-(2-(dimethylamino)ethylamino)anthracene-9,10-dione) | Mitochondria |
| 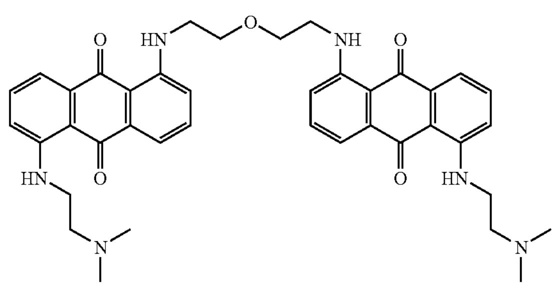 [SMILES: CN(C)CCNc1cccc2c1C(=O)c1cccc(NCCOCCNc3cccc4c3C(=O)c3cccc(NCCN(C)C)c3C4=O)c1C2=O] | Compound 30 | 5,5'-(2,2'-oxybis(ethane-2,1-diyl)bis(azanediyl))bis-(1-(2-(dimethylamino)ethylamino)anthracene-9,10-dione) | Vesicle |
| 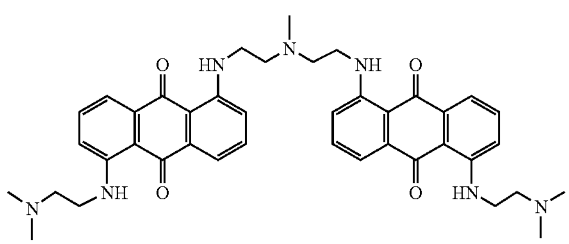 | Compound 31 | 5,5'-(2,2'-(methylazanediyl)-bis(ethane-2,1 diyl)bis(azanediyl))bis(1-(2-(dimethylamino)ethylamino)anthracene-9,10-dione) | Nucleus |
| 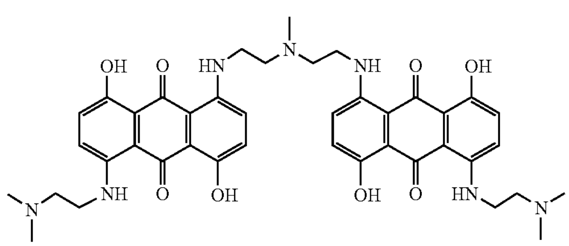 | Compound 32 | 8,8'-(2,2'-(methylazanediyl)-bis(ethane-2,1 diyl)bis(azanediyl))bis(4-(2-(dimethylamino)ethylamin)-1,5-dihydroxyanthracen-9,10-dione) | Nucleus |

TABLE 5-continued

Examples of Organelle-Targeting Fluorochromes

| STRUCTURE | DESIGNATION | CHEMICAL NAME | PRIMARY TARGET |
|---|---|---|---|
| (structure) | Compound 33 | 5,5'-(3,3'-(methylazanediyl)bis-(propne-3,1-diyl)bis(azanediyl))bis(1-(2-(dimethylamino)ethylamin)-anthracen-9,10-dione) | Nucleus |

TABLE 6

Cross-Reference of Compounds

| Compound No. | Intermediary (Yes) | Example No. | Organelle |
|---|---|---|---|
| 1 |  | 1, 20, 21, 24 | lysosome |
| 6 | Yes for 7 | 4 |  |
| 7 |  | 4 | lysosome |
| 11 |  | 8, 22, 23, 25, 26 | nucleus |
| 19 |  | 13, 25, 26 | nucleus |
| 17 | Yes for 18, 22, 23, 29, 30, 31 & 33 | 13 |  |
| 18 | Yes for 19 | 13 |  |
| 15 |  | 12 | nucleus |
| 16 | Yes for 20 | 12 | nucleus |
| 20 |  | 14 | nucleus |
| 8 |  | 5 | cytosol + nucleus |
| 9 |  | 6 |  |
| 10 |  | 7, 25, 26 | Cytosol + mitochondria |
| 2 |  | 2 | Golgi |
| 3 |  | 2 | Golgi |
| 4 |  | 3 | Total Cell Stain |
| 5 |  | 3 | Total Cell Stain |
| 21 | Yes for 22 | 15 |  |
| 22 |  | 15 | Total Cell Stain |
| 12 |  | 9 | Total Cell Stain |
| 24 |  | 16 | Total Cell Stain |
| 23 | Yes for 24 | 16 |  |
| 25 | Yes for 26 | 17 |  |
| 26 |  | 17 | Total Cell Stain |
| 13 | Yes for 32 | 10 | Vesicle |
| 14 |  | 11 | nucleus |
| 27 | Yes for 28 | 18 |  |
| 28 |  | 18 | Vesicle |
| 29 |  | 19 | Mitochondria |
| 30 |  | 20 | Vesicle |
| 31 |  | 21 | Nucleus |
| 32 |  | 22 | Nucleus |
| 33 |  | 23 | Nucleus |

Example 1

Synthesis of 1,4-bis(2-(dimethylamino)ethylamino)-2,3-difluoro-5,8-dihydroxyanthracene-9,10-dione (Compound 1)

A mixture of 1,2,3,4-tetrafluoro-5,8-dihydroxyanthraquinone (1.0 g, 3.2 mmol) and N,N-dimethylethylenediamine (3 mL) in $CH_2Cl_2$ (30 mL) was stirred at room temperature for 12 hours. After evaporation of the solvents, the residue was purified by silica gel chromatography using isocratic solvent system of $EtOAc/MeOH/Et_3N$ (10:10:1) yielding 830 mgs of Compound 1 as dark blue product. Abs (max, PBS pH 7.4)=568 nm; Em=675 nm. The structure of Compound 1 is given below:

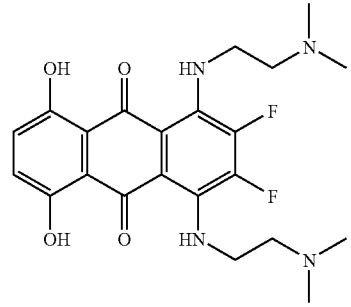 [SMILES: CN(C)CCNc1c(F)c(F)c(NCCN(C)C)c2c1C(=O)c1c(O)ccc(O)c1C2=O]

Example 2

Synthesis of trifluoro-anthraquinone ceramide (Compound 2) and difluoro-anthraquinone ceramide (Compound 3)

A mixture of 1,2,3,4-tetrafluoro-5,8-dihydroxyanthraquinone (62.4 mg, 10.2 mmol), D-sphingosine (123 mg, 0.4 mmol) in $CH_2Cl_2$ (8 mL) was stirred at room temperature for 12 h. After evaporation of the solvents, the residue was purified on silica gel chromatography eluted with $EtOAc/MeOH/Et_3N$ (10:10:1) to afford monoamine substituted Compound 2 (115 mg) and diamine substituted Compound 3 (34 mg). Abs (max, PBS pH 7.4)=533 nm; Em=625 nm for Compound 2 and Abs (max, PBS pH 7.4)=572 nm; Em=697 nm for Compound 3. The structures of these compounds are given below:

Compound 2

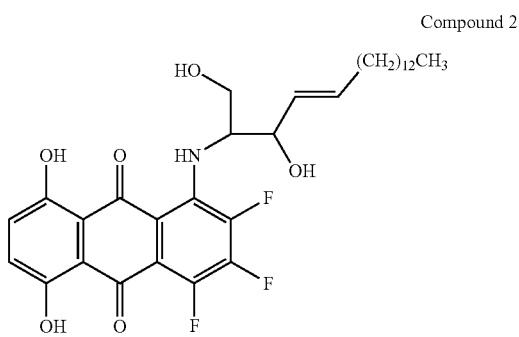

Example 3

Synthesis of 1,2,3-trifluoro-5,8-dihydroxy-4-(2-(2-hydroxyethylamino)ethylamino)anthreacene-9,10-dione (Compound 4) and 2,3-difluoro-5,8-dihydroxy1,4-bis(2-(2-hydroxyethylamino)ethylamino) anthreacene-9,10-dione (Compound 5)

A mixture of 1,2,3,4-tetrafluoro-5,8-dihydroxyanthraquinone (1.0 g, 3.2 mmol) and 2-(2-aminoethylamino) ethanol (3.26 mL, 32 mmol) in $CH_2Cl_2$ (20 mL) was stirred at room temperature for 12 hours. After evaporation of the solvents, the residue was purified by silica gel chromatography using isocratic solvent system of $EtOAc/MeOH/Et_3N$ (10:10:1) yielding 200 mg of Compound 4 and 350 mg of Compound 5. Abs (max, PBS pH 7.4)=593 nm for Compound 4 and Abs (max, PBS pH 7.4)=574 nm for Compound 5. The structures of these compounds are given below:

Compound 4

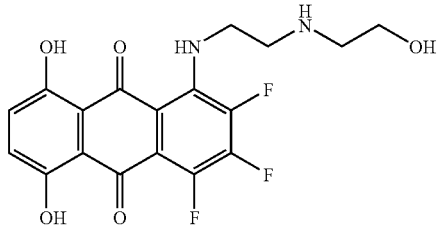

Compound 5

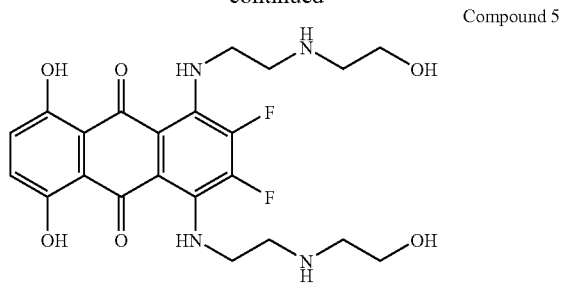

Example 4

Synthesis of Compound 7 a) Preparation of 1,8-bis(2-(dimethylamino)ethylamino)anthracene-9,10-dione (Compound 6)

A mixture of 1,8-dichloroanthraquinone (5.5 g, 20 mmol) and N,N-dimethylethylenediamine (40 mL) was refluxed for 18 h. The mixture was cooled to room temperature and diluted with water to precipitate the title compound which was recrystallised from methanol to afford Compound 6 (4.5 g). The structure of Compound 6 is given below:

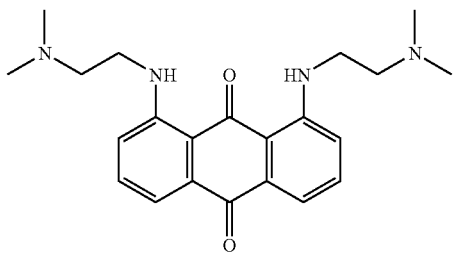

b) Preparation of 1,8-bis(2-(dimethylamino)ethylamino)-4,5-dihydroxyanthracene-9,10-dione (Compound 7)

The anthracene-9,10-dione derivative (Compound 6, 1.0 g, 2.6 mmol) was dissolved in 10 ml of concentrated $H_2SO_4$ and cooled to −10° C. Anhydrous sodium chlorate (1.1 g, 10.4 mmol) was added in portions over 1.5 h and the mixture then stirred for 12 h at room temperature. The blue solution was added slowly to a cold sodium hydrogen sulfite solution (1%, 160 mL). The mixture was neutralized to pH 7 with 5 M NaOH. The titled compound was extracted from the aqueous phrase with $CH_2Cl_2$ and concentrated in vacuum. Silica gel Column chromatography ($CH_2Cl_2$/MeOH: 9:1) gave Compound 7 (270 mg). Abs (max, PBS pH 7.4)=571 nm; Em=647 nm. The structure of Compound 7 is given below:

Compound 3

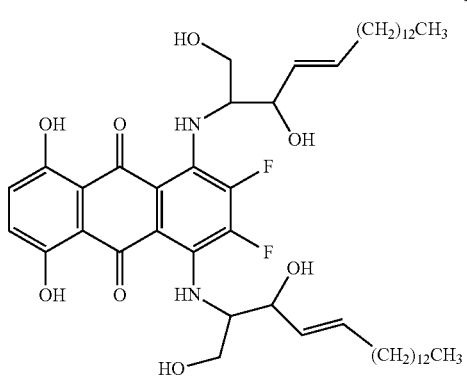

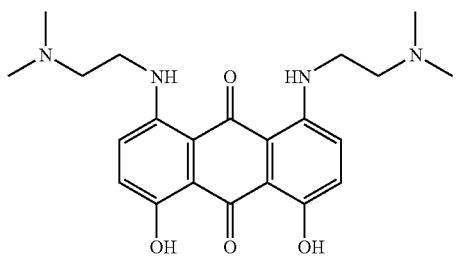

Example 5

Synthesis of 1,1'-(dihydroxy-9,10-dioxo-9,10-dihydro anthracene-1,5-diyl)bis(3,3-dimethyl thiourea)

(Compound 8)

A mixture of 1,5-diamino-4,8-dihydroxyanthraquinone (0.54 g, 2 mmols), Imidazole (1.34 g, 20 mmols), tert-butyldimethylsilyl chloride (0.66 g, 4.4 mmols) and 20 ml of MeCONMe$_2$) was heated at 120° C. for 2 hours. Dimethylthiocarbamoyl chloride (0.31 g, 2.5 mmols) was then added and the reaction mixture was stirred at 120° C. for another 2 hours. Upon cooling to room temperature, n-Bu4N+F (5 ml, 1 M in THF) was added and the mixture was stirred for 1 hour. It was then concentrated in the rotary evaporator and purified by silica gel chromatography (5% of MeOH in CH$_2$Cl$_2$), yielding 60 mg of Compound 8 as a reddish solid. Abs (max, PBS pH 7.4)=629 nm; Em=669 nm. The structure of Compound 8 is given below:

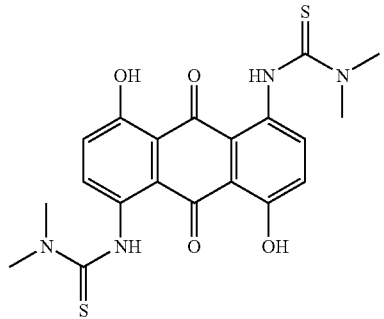

Example 6

Synthesis of 1,5-bis((2-(dimethylamino)ethyl)(methyl)amino)anthracene-9,10-dione (Compound 9)

A mixture of 1,5-dichloroanthraquinone (5.5 g, 20 mmol) and N,N,N'-trimethylethylenediamine (40 ml) was refluxed for 18 h. The mixture was cooled to room temperature, diluted with water (400 mL) and extracted with chloroform (2×200 mL). The combined organic layer was washed with water, brine, dried over MgSO$_4$ and evaporated to dryness. The residue thus obtained was purified by silica gel flash chromatography [CHCl$_3$/MeOH/Et$_3$N (44:5:1)] to provide Compound 9. Abs (max, PBS pH 7.4)=508 nm. The structure of Compound 9 is given below:

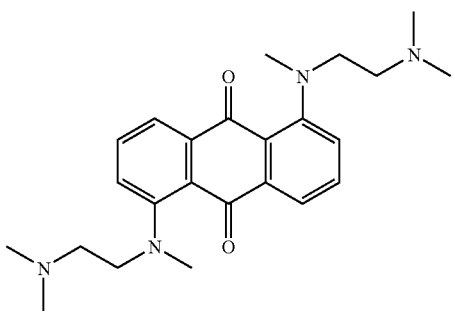

Example 7

Synthesis of O,O'-4,8-bis(3,3-dimethylthioureido)-9,10-dioxo-9,10-dihydroanthracene-1,5-diyl bis(dimethyl carbamothioate) (Compound 10)

A mixture of 1,5-diamino-4,8-dihydroxyanthraquinone (0.54 g, 2 mmols), dimethylthiocarbamoyl chloride (1.5 g, 12 mmols), and 15 ml of MeCONMe$_2$ was heated at 100° C. overnight. The reaction mixture was concentrated and purified by silica gel chromatography eluted (3% of MeOH in CH$_2$Cl$_2$) to yield 320 mg of Compound 10. Abs (max, PBS pH 7.4)=516 nm; Em=613 nm. The structure of Compound 10 is given below:

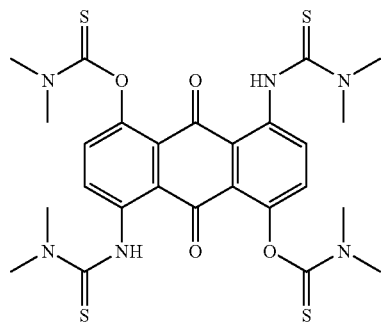

Example 8

Synthesis of 1,5-bis(4-methylpiperazin-1-yl)anthracene-9,10-dione (Compound 11)

A mixture of 1,5-dichloroanthraquinone (4.00 g, 14.7 mmol) and 1-methylpiparazine (14.72 g, 147 mmol) was refluxed for 17 hours. The mixture was cooled to room temperature and diluted with water (100 mL) to precipitate the title compound. The brick red solid obtained was collected by filtration, washed with excess water and ether and dried under vacuum to afford 4.28 g of Compound 11. Abs (max, in water)=475 nm. The structure of Compound 11 is given below:

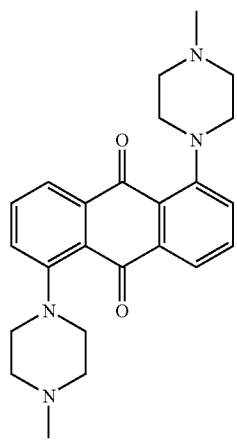 [SMILES: CN1CCN(c2cccc3c2C(=O)c2cccc(N4CCN(C)CC4)c2C3=O)CC1]

Example 9

Synthesis of bis(2-dimethylamino)ethyl)3,3'-(4,8-dihydroxy-9,10-dioxo-9,10-dihydroanthracene-1,5-diyl)bis(azanediyl)dipropanoate (Compound 12)

A mixture of 1,5-diamino-4,8-dihydroxyanthraquinone (1.08 g, 4 mmols), 2-(dimethylamino)ethyl acrylate (1.52 ml, 10 mmols) and 10 mL of MeCONMe$_2$ was heated at 100° C. for 50 hours. The reaction mixture was concentrated and purified by silica gel chromatography (20% of MeOH in CH$_2$Cl$_2$), yielding 125 mg of Compound 12. Abs (max, PBS pH 7.4)=610 nm; Em=705 nm. The structure of Compound 12 is given below:

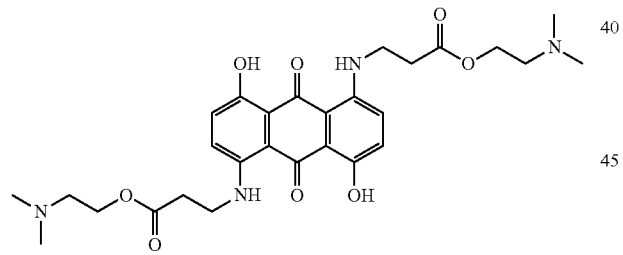

Example 10

Synthesis of 1,5-bis(3-(diethyl phosphoryl)propylamino)-4,8-dihydroxyanthracene-9,10-dione (Compound 13)

A mixture of 1,5-diamino-4,8-dihydroxyanthraquinone (0.54 g, 2 mmols), Diethyl-(3-bromopropyl)phosphonate (1.15 ml, 6 mmols) and 15 ml of MeCONMe$_2$ was refluxed overnight. The reaction mixture was concentrated and purified by silica gel chromatography eluted with CH$_2$Cl$_2$ to yielding 420 mgs of compound x-v-53. Abs (max, PBS pH 7.4)=665 nm; Em=710 nm. The structure of Compound 13 is given below:

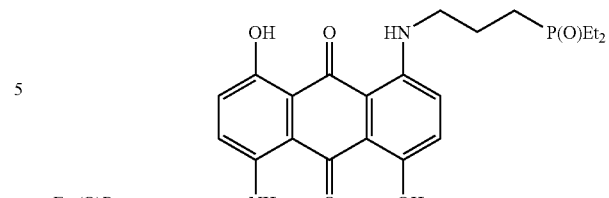

Example 11

Synthesis of Compound 14

A mixture of 1,5-dichloroanthracene-9,10-dione (0.83 g, 3 mmol), dimethylaminoethylenehydrazine [which was prepared from dimethylaminoethylenehydrazine dihydrochloride (1.76 g, 10 mmol) and NaOH (0.4 g, 10 mmol) in 5 ml of H$_2$O] and MeCONMe$_2$ (15 mL) was refluxed for 12 hours. After evaporation of the solvents, the residue was purified by silica gel chromatography (10% MeOH in CH$_2$Cl$_2$) yielding Compound 14 (620 mg) as a yellow product. Abs (max, PBS pH 7.4)=415 nm; Em=498 nm. The structure of Compound 14 is given below:

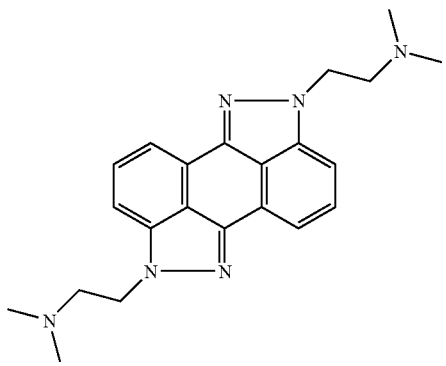

Example 12

Synthesis of 1,5-bis(2-(dimethylamino)ethylamino)-4-nitroanthracene-9,10-dione (Compound 15) and 1,5-bis(2-(dimethylamino)ethylamino)-4,8-dinitroanthracene-9,10-dione (Compound 16))

A solution of 1,5-bis(2-(dimethylamino)ethylamino)anthracene-9,10-dione (500 mg, 1.32 mmol) (prepared according to U.S. Pat. No. 6,468,753) in 8 mL of nitric acid (>90%) was heated at 40° C. for 3 h. The mixture was cooled to room temperature, diluted with 25 ml of water and neutralized to pH 7-8 with 5 N NaOH. The mixture was concentrated and purified on silica column chromatography (CH$_2$Cl$_2$/MeOH: 9:1) to afford Compound 15 (120 mg) and Compound 16 (52 mg). Abs (max, PBS pH 7.4)=586 nm for Compound 15 and 598 nm for Compound 16. The structure of Compounds 15 and 16 are given below:

Compound 15

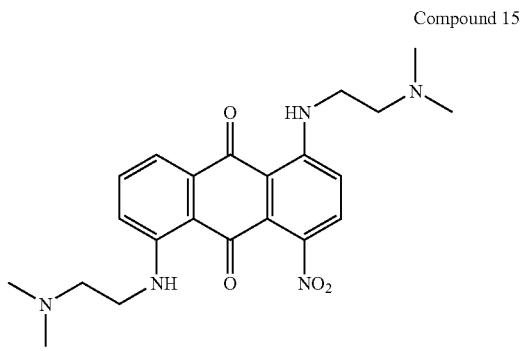

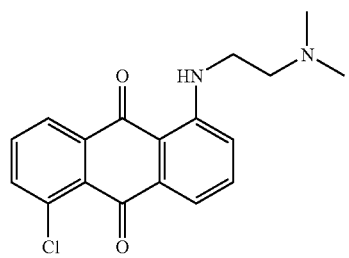 [SMILES: CN(C)CCNc1cccc2c1C(=O)c1cccc(Cl)c1C2=O]

b) Preparation of 1-(2-(dimethylamino)ethylamino)-5-(4-methylpiperazin-1-yl)anthracene-9,10-dione (Compound 18)

A mixture of Compound 17 (1.0 g, 3.0 mmol) and 1-methylpiparazine (1.5 g, 15.0 mmol) was refluxed for 17 hours. The mixture was cooled to room temperature, dissolved in 100 mL $CH_2Cl_2$ and extracted with water and brine. The organic layer was dried ($Na_2SO_4$) and evaporated to provide Compound 18 (540 mg). This product was used in the next step without any purification. $R_f$ (9:1 $CHCl_3$/MeOH): 0.15. The structure of Compound 18 is given below:

Compound 16

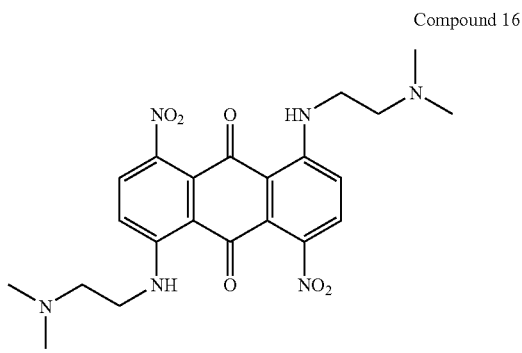

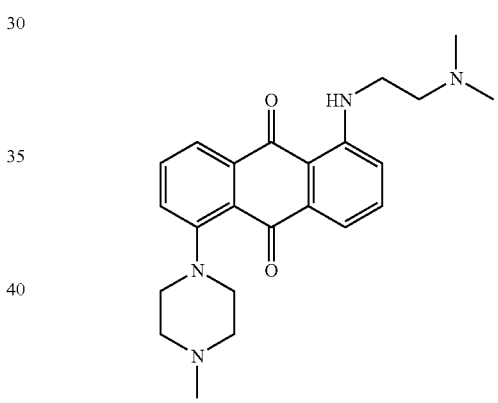

Example 13

Synthesis of 1-(2-dimethylamino)ethylamino)-4-hydroxy-5-(4-methylpiperazin-1-yl)anthracene-9,10-dione (Compound 19)

a) Preparation of 1-Chloro-5-(2-(dimethylamino)ethylamino)anthracene-9,10-dione (Compound 17)

A mixture of 1,5-dichloro anthraquinone (5.0 g, 18.0 mmol), N,N-dimethylacetamide (30 mL) and N,N-dimethylethylenediamine (2 mL, 18 mmol) was stirred at room temperature for 1 hour and then heated in an oil bath (T=100° C.) for 45 minutes. Reaction mixture was cooled and filtered. To the filtrate petroleum ether (50 mL) was added and combined mixture was stirred at 4° C. over night. Precipitated solid was removed by filtration and supernatant was evaporated to dryness, co-evaporated with chloroform and dried under vacuum. The crude dye was then purified on Biotage SP4 system using a gradient of methanol in chloroform. Appropriate fractions were combined and evaporated to dryness to provide Compound 17 (1.0 g) as a red solid. $R_f$ (9:1 $CHCl_3$/MeOH): 0.46; Abs (max, PBS)=500 nm. The structure of Compound 17 is given below:

c) Preparation of Compound 19

Compound 18 (0.54 g, 1.4 mmol) was dissolved in 4 mL of concentrated $H_2SO_4$ and cooled to –10° C. (ice/salt mixture). Anhydrous sodium chlorate (0.6 g, 5.6 mmol) was added in portions over 1.5 h and the mixture was stirred at room temperature for 22 h. The dark colored solution was added slowly to a cold sodium hydrogen sulfite solution (1%, 75 mL) and the mixture was neutralized to pH 7 with 10M aqueous NaOH. The aqueous phase was extracted with $CH_2Cl_2$ (150 mL) and then the organic phase was washed with water, brine, dried ($Na_2SO_4$) and evaporated to dryness. The crude dye thus obtained was purified on Biotage SP4 system using a gradient of methanol in chloroform (7% to 60% over 10 column volume). Appropriate fractions were combined and evaporated to dryness to provide Compound 19 (50 mg) as a blue solid. $R_f$ (7:3 $CHCl_3$/MeOH): 0.31; Abs (max, PBS) =525 and 600 nm; Em (max, PBS)=648 nm. The structure of Compound 19 is given below:

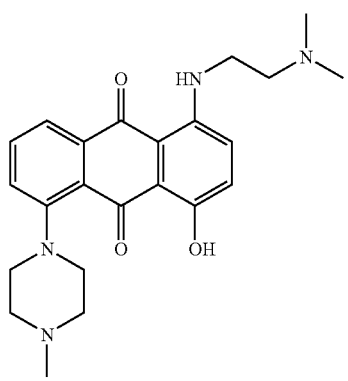 [SMILES: CN(C)CCNc1ccc(O)c2c1C(=O)c1cccc(N3CCN(C)CC3)c1C2=O]

Example 14

Synthesis of 1,5-diamino-4,8-bis(2-(dimethylamino) ethyl amino)anthracene-9,10-dione (Compound 20)

A mixture of Compound 16 (25 mg) and concentrated HCl (2 ml) was cooled to 0° C. and then 50 mg of SnCl$_2$ was added. The combined mixture was stirred at 0° C. for 30 min and then warmed to room temperature for 5 hours. The mixture was then neutralized with 5 M NaOH and concentrated. The residue was purified by silica gel chromatography eluted (20% methanol in methylene chloride) to yield 15 mg of Compound 20. Abs (max, PBS pH 7.4)=690 nm. The structure of Compound 20 is given below:

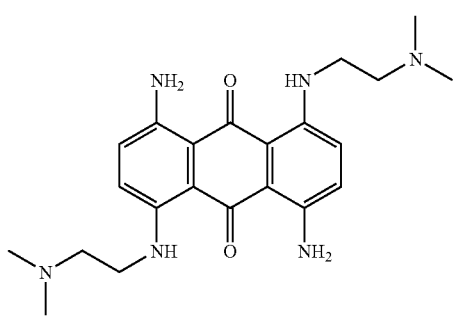

Example 15

Synthesis of 1-(2-(dimethylamino)ethylamino-4,8-dihydroxy-5-(2-hydroxy ethylamino)anthracene-9,10-dione (Compound 22)

a) Preparation of 1-(2-(dimethylamino)ethylamino)-5-(2-hydroxyl ethylamino)anthracene-9,10-dione (Compound 21)

A mixture of Compound 17 (0.87 g, 2.7 mmol) and ethanolamine (0.8 mL, 13.23 mmol) was heated in an oil bath (~150° C.) for 18 hours. The mixture was cooled to room temperature, dissolved in 100 mL CH$_2$Cl$_2$ and extracted with water and brine. The organic layer was dried (Na$_2$SO$_4$) and evaporated to provide Compound 21 (370 mg). This product was used in the next step without any purification. R$_f$ (9:1 CHCl$_3$/MeOH): 0.19. The structure of Compound 21 is given below:

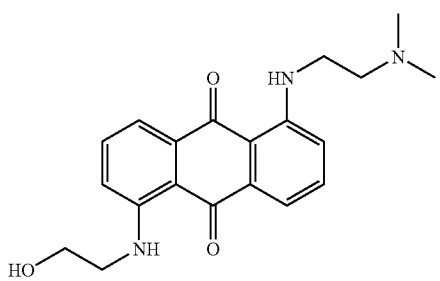 [SMILES: CN(C)CCNc1cccc2c1C(=O)c1cccc(NCCO)c1C2=O]

b) Preparation of Compound 22

This procedure was carried out as described previously in step (c) of Example 13, using Compound 21 (0.37 g, 1.05 mmol), NaClO$_3$ (0.45 g, 4.19 mmol) and conc H$_2$SO$_4$ (5 mL). The crude dye obtained was purified on Biotage (Flash 25+M) using a gradient of 2% to 20% methanol over 15 column volume. The dye was obtained as a blue solid (15 mg). The structure of Compound 22 is given below:

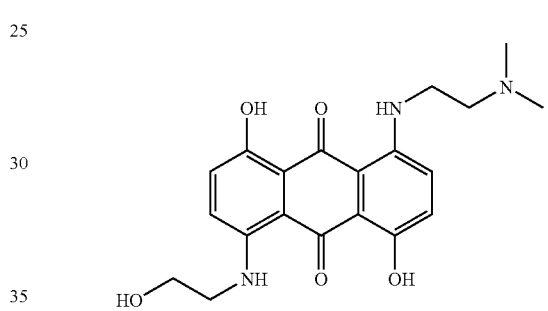

Example 16

Synthesis of 1-(2-(dimethylamino)ethylamino-4,8-dihydroxy-5-(2-methoxy ethylamino)anthracene-9,10-dione (Compound 24)

a) Preparation of 1-(2-(dimethylamino)ethylamino-5-(2-methoxy ethylamino)anthracene-9,10-dione (Compound 23)

This procedure was carried out as described previously in step (a) of Example 15, using Compound 17 (0.25 g, 0.76 mmol) and 2-methoxyethylamin (0.66 mL, 7.6 mmol). This product was used in the next step without any purification. The structure of Compound 23 is given below:

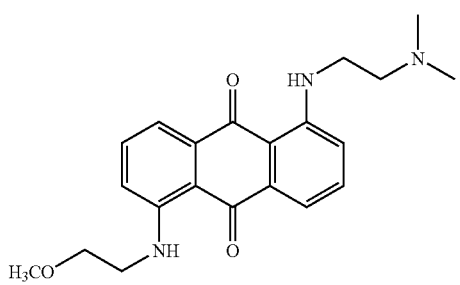 [SMILES: COCCNc1cccc2c1C(=O)c1cccc(NCCN(C)C)c1C2=O]

b) Preparation of Compound 24

This procedure was carried out as described previously in step (c) of Example 13, using Compound 23 (0.22 g, 0.61 mmol), NaClO$_3$ (0.26 g, 2.44 mmol) and conc H$_2$SO$_4$ (3 mL). The crude dye obtained was purified on Biotage (Flash 25+M) using a gradient of 2% to 20% methanol over 15 column volume. The dye was obtained as a blue solid (40 mg). The structure of Compound 24 is given below:

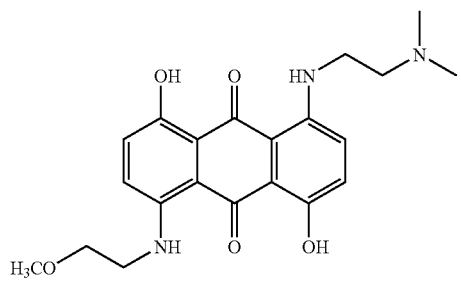 [SMILES: COCCNc1ccc(O)c2c1C(=O)c1c(O)ccc(NCCN(C)C)c1C2=O]

Example 17

Synthesis of 1,5-dihydroxy-4,8-bis(2-methoxyethyl amino)anthracene-9,10-dione (Compound 26)

a) Preparation of 1,5-bis(2-methoxyethylamino)anthracene-9,10-dione (Compound 25)

This procedure was carried out as described previously in Example 8, using 1,5-dichloroanthraquinone (2.0 g, 7.22 mmol) and 2-methoxyethylamine (6.23 mL, 72.2 mmol). The dye was obtained as a red solid (2.39 g). The structure of Compound 26 is given below:

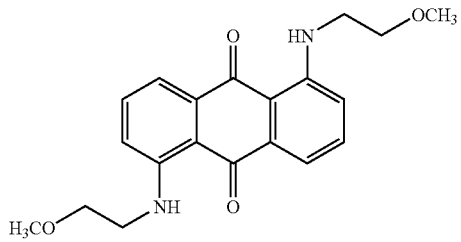 [SMILES: COCCNc1cccc2c1C(=O)c1cccc(NCCOC)c1C2=O]

b) Preparation of Compound 26

This procedure was carried out as described previously in step (c) of Example 13, using Compound 26 (0.5 g, 1.41 mmol), NaClO$_3$ (0.6 g, 5.64 mmol) and conc H$_2$SO$_4$ (5 mL). The crude dye obtained was purified by preparative TLC (hexane:ethyl acetate=1:1). The dye was obtained as a blue solid (9 mg). The structure of Compound 26 is given below:

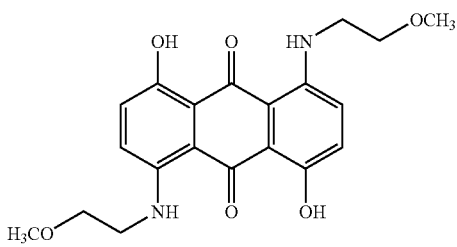 [SMILES: COCCNc1ccc(O)c2c1C(=O)c1c(O)ccc(NCCOC)c1C2=O]

Example 18

Synthesis of 1,5-dihydroxy-4,8-bis(pyridin-3-ylamino)anthracene-9,10-dione (Compound 28)

a) Preparation of 1,5-bis(pyridin-3-ylamino)anthracene-9,10-dione (Compound 27)

Potassium t-butoxide (3.37 g, 30 mmol) and Pd$_2$(dba)$_3$ (0.55 g, 0.6 mmol) were added to a 100 mL round bottom flask. Toluene (50 mL) and triisobutylphosphatrane (0.82 g, 2.4 mmol) were then added, followed by 3-aminopyridine (1.88 g, 20 mmol) and 1,5-dichloroanthraquinone (2.77 g, 10 mmol). The system was flushed with argon and heated to reflux overnight. The mixture was cooled and the solvent was removed under vacuum. The residue was dissolved in dichloromethane and water. The organic layer was washed with water twice and dried over anhydrous magnesium sulfate. After the solvent was removed, the residue was purified by flash chromatography to provide Compound 27 as a red solid. The structure of Compound 27 is given below:

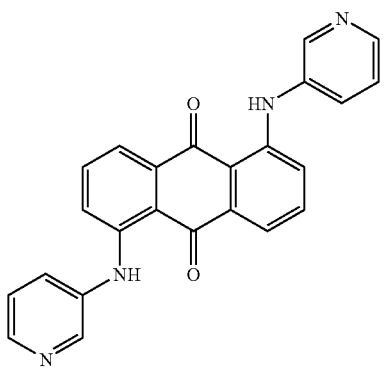 [SMILES: O=C1c2cccc(Nc3cccnc3)c2C(=O)c2cccc(Nc3cccnc3)c21]

b) Preparation of Compound 28

This procedure was carried out as described previously in step (c) of Example 13, using Compound 27 (0.4 g, 1.02 mmol), NaClO$_3$ (0.43 g, 4.07 mmol) and conc H$_2$SO$_4$ (3 mL). The crude dye obtained was purified by by flash chromatography. The dye was obtained as a blue solid (6 mg). The structure of Compound 28 is given below:

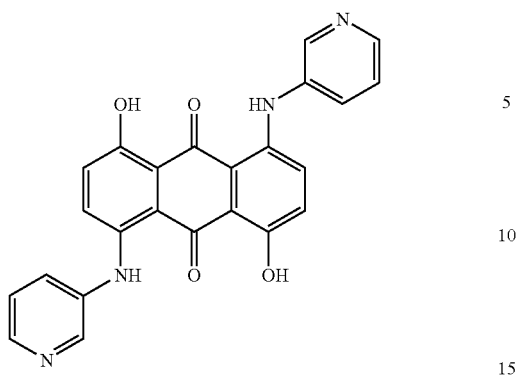

Example 19

Synthesis of 5,5'-(3,3'-oxy bis(ethane-2,2-diyl)bis (oxy))bis(propane-3,1-diyl)bis(1-(2-(dimethylamino) ethylamino)anthracene-9,10-dione) (Compound 29)

A mixture of Compound 17 (0.2 g, 0.61 mmol) and 4,7,10-trioxa-1,13-tridecane diamine (0.134 g, 134 µL, 0.61 mmol) was heated at 150° C. for 20 hours. The mixture was cooled to room temperature, dissolved in 10 mL CHCl$_3$ and purified on Biotage (Flash 25+M) using a gradient of 5% to 30% methanol in chloroform. The dye was obtained as a red solid (64 mg); Abs (max, PBS)=530 and 285 nm; Em (max, PBS)=655 nm. The structure of Compound 29 is given below:

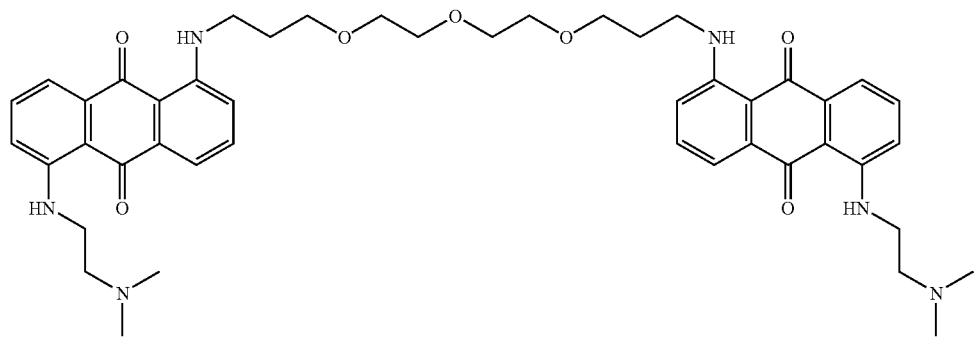 [SMILES: CN(C)CCNc1cccc2c1C(=O)c1cccc(NCCCOCCOCCOCCCNc3cccc4c3C(=O)c3cccc(NCCN(C)C)c3C4=O)c1C2=O]

Example 20

Synthesis of 5,5'-(2,2'-oxybis(ethane-2,1-diyl)bis (azanediyl))bis(1-(2-(dimethylamino)ethylamino) anthracene-9,10-dione) (Compound 30)

This procedure was carried out as described previously in Example 19, using Compound 17 (187 mg, 0.57 mmol) and 2,2'-oxybis(ethylamine) (61 µL, 0.57 mmol). The dye was obtained as a red solid (50 mg) after Biotage purification using a gradient of methanol in chloroform. The structure of Compound 30 is given below:

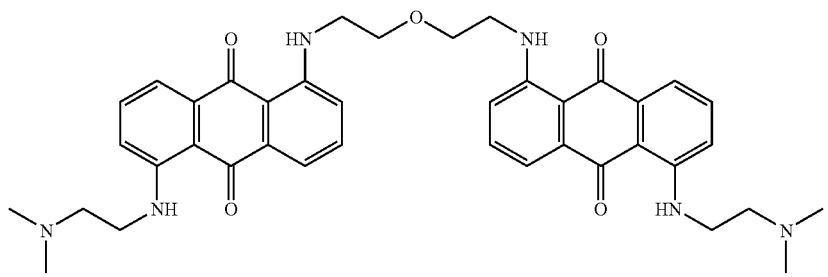

Example 21

Synthesis of 5,5'-(2,2'-(methylazanediyl)bis(ethane-2,1-diyl)bis(azanediyl))bis(1-(2-(dimethylamino) ethylamino)anthracene-9,10-dione) (Compound 31)

This procedure was carried out as described previously in Example 19, using Compound 17 (545 mg, 1.66 mmol) and N-methyl-2,2'-diaminodiethylamine (214 μL, 1.66 mmol). The dye was obtained as a red solid (270 mg) after Biotage purification using a gradient of methanol in chloroform. The structure of Compound 31 is given below:

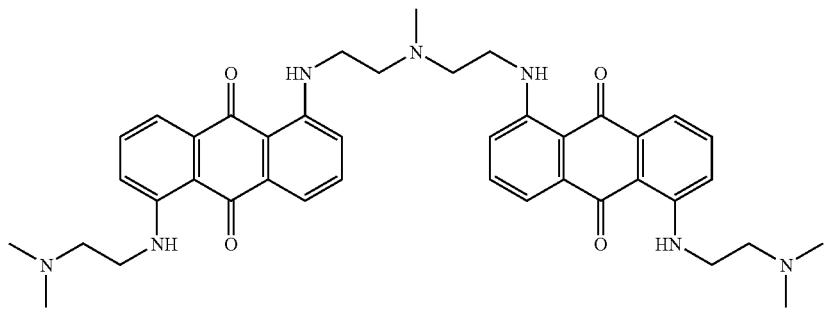

Example 22

Synthesis of 8,8'-(2,2'-(methylazanediyl)bis(ethane-2,1-diyl)bis(azanediyl))bis(4-(2-(dimethylamino) ethylamino)-1,5-dihydroxyanthracen-9,10-dione) (Compound 32)

This procedure was carried out as described previously in step (c) of Example 13, using Compound 31 (0.27 g, 0.39 mmol), $NaClO_3$ (0.33 g, 3.1 mmol) and conc $H_2SO_4$ (6 mL). The crude dye obtained was purified on Biotage (Flash 25+M) using a gradient of 2% to 20% methanol over 15 column volume. The dye was obtained as a blue solid (25 mg). The structure of Compound 32 is given below:

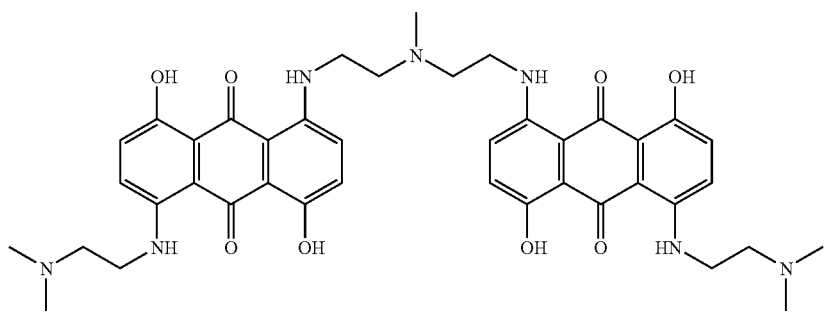

Example 23

Synthesis of 5,5'-(3,3'-(methylazanediyl)bis(propane-3,1-diyl)bis(azanediyl))bis(1-(2-(dimethylamino)ethylamino)-anthracen-9,10-dione) (Compound 33)

This procedure was carried out as described previously in Example 19, using Compound 17 (520 mg, 1.58 mmol) and N,N-bis(3-aminopropyl)methylamine (383 μL, 2.37 mmol). The dye was obtained as a red solid (250 mg) after Biotage purification using a gradient of methanol in chloroform. The structure of Compound 33 is given below:

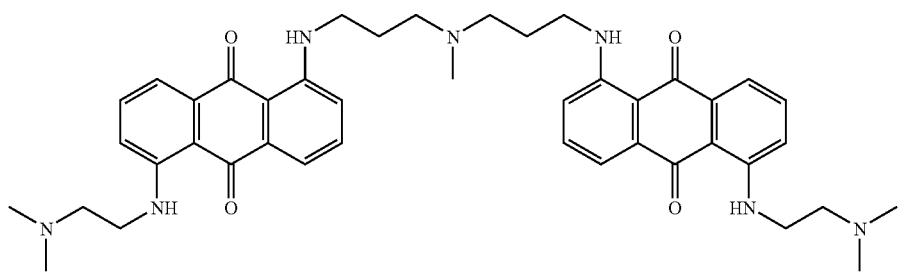

Example 24

Staining of Lysosomes in Various Live Mammalian Cells, Using Compound 1

Cell cultures were maintained in an incubator at 37° C., with 5% $CO_2$ atmosphere. Human cervical adenocarcinoma epithelial cell line HeLa (ATTC, Manassas, Va.) was routinely cultured in Dulbecco's modified eagle medium with low Glucose (Sigma-Aldrich, St. Louis, Mo.), supplemented with 10% fetal bovine serum heat inactivated (Sigma), 0.25 ug/ml fungizone (Invitrogen Corp., Carlsbad, Calif.), 100 U/ml penicillin, 100 ug/ml streptomycin (Invitrogen) and 1% MEM Non-essential amino acids (Invitrogen). Chinese hamster ovary epithelial cell line CHO-K1 was obtained from ATCC. CHO-K1 cells were cultured in ATCC-formulated F12K medium supplemented with 10% fetal bovine serum heat inactivated (Sigma), 0.25 ug/ml fungizone (Invitrogen), 100 U/ml penicillin and 100 μg/ml streptomycin (Invitrogen). Human bone osteosarcoma epithelial cell line, U2-OS was obtained from ATCC and cells were cultured in McCoy's 5a medium ATCC-modified supplemented with 10% fetal bovine serum heat inactivated (Sigma), 0.25 ug/ml fungizone (Invitrogen), 100 U/ml penicillin and 100 ug/ml streptomycin (Invitrogen).

Compound 1 was dissolved in 0.005 N HCl to a 5 mM final stock concentration. For cell imaging, Compound 1 was added to culture media and cells were incubated for 15 min at ambient temperature or 37° C. in a cell culture incubator 5% $CO_2$ atmosphere. The media was removed and cells were washed 3 times with fresh medium. Cells were then imaged in phosphate-buffered saline (PBS) at ambient temperature. Imaging was performed using an Olympus BX51 microscope (60× objective). Exposure times were generally adjusted to around one sec. The microscope was equipped with Fluorescence Mirror units: set 41001 (Exciter: 480, Emitter: 535) for green detection (FITC); Set 41002c (Exciter: 545, Emitter: 620) for TRITC (Rhodamine with narrow-band excitation filter) red shifted emission; Filter set 41004 (Exciter 560, Emitter 645) for Texas Red emission; Set 41008 (Exciter: 620, Emitter 700,) for Cy5 emission. All filter sets were from Chroma Technology Corp, Rockingham, Vt.).

Titration of Compound 1 on Hela Cells indicated that 10 uM was the optimum concentration to stain lysosomes after 10 to 15 min incubation at room temperature or 37° C. As demonstrated in FIG. 3, Compound 1 localized to the lysosomes of all three cell lines evaluated. Similar experimental results were achieved using Compound 7.

Example 25

Figure 4:
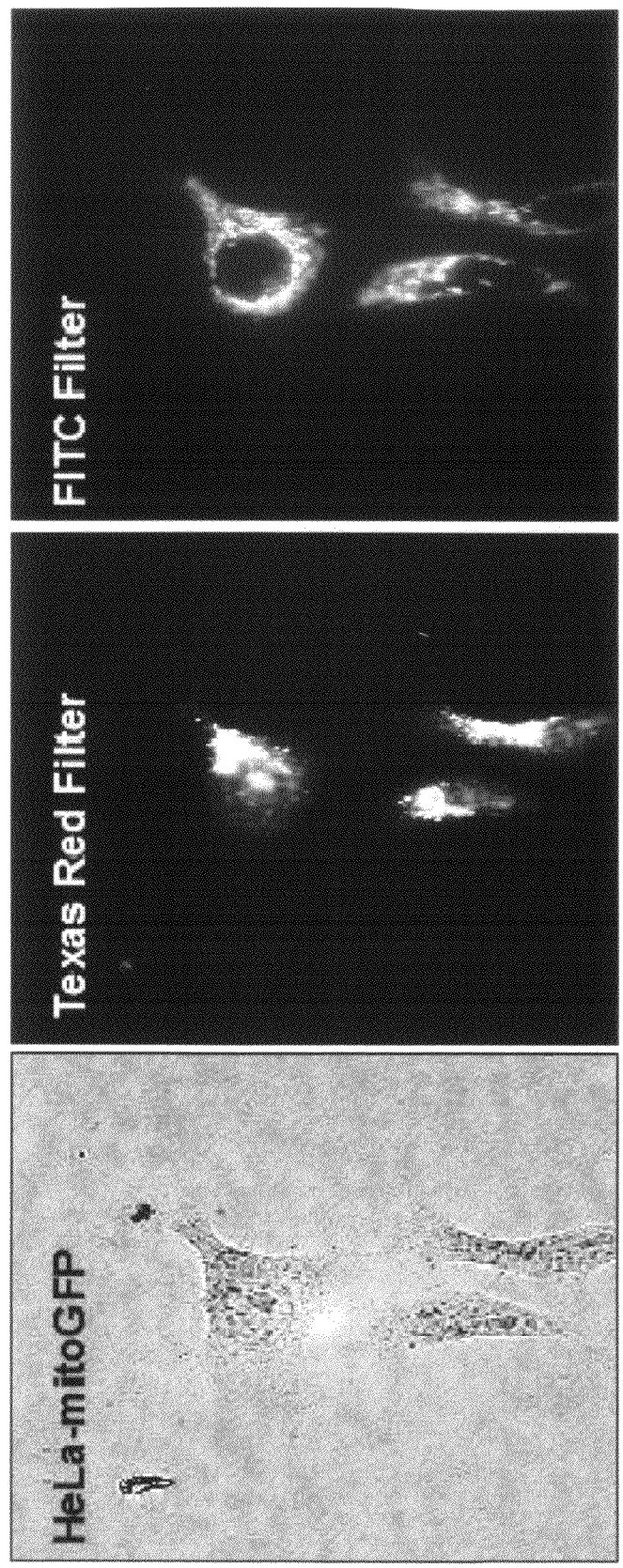
FIG. 4: Counter-staining lysosomes in GFP-expressing cells with an anthraquinone fluorochrome.

Performance Advantages of Compound 1 Relative to Lysotracker Red DND-99 and Acridine Orange for the Selective Labeling of Lysosomes in GFP-Expressing Cells The HeLa-TurboGreen-mitochondria (HeLa-mitoGFP, MarinPharm GmbH, Luckenwalde, Germany) cell line expresses EGFP-cytochrome oxidase chimeric proteins that are primarily localized to the mitochondria. The cells were cultivated as described in Example 17 for standard HeLa cells. After incubation of these cells with compound 1, as described in example 17, lysosomes and mitochondria were independently imaged on an Olympus BX51 microscope (60× objective). Fluorescence signals from compound 1 and GFP were readily distinguished using the Texas Red and FITC filters, as shown in FIG. 4. Control HeLa cells, not expressing GFP, displayed no fluorescence signal in the FITC window, while HeLa-mitoGFP cells, not treated with Compound 1, displayed no fluorescence signal in the Texas Red window.

Figure 5A:
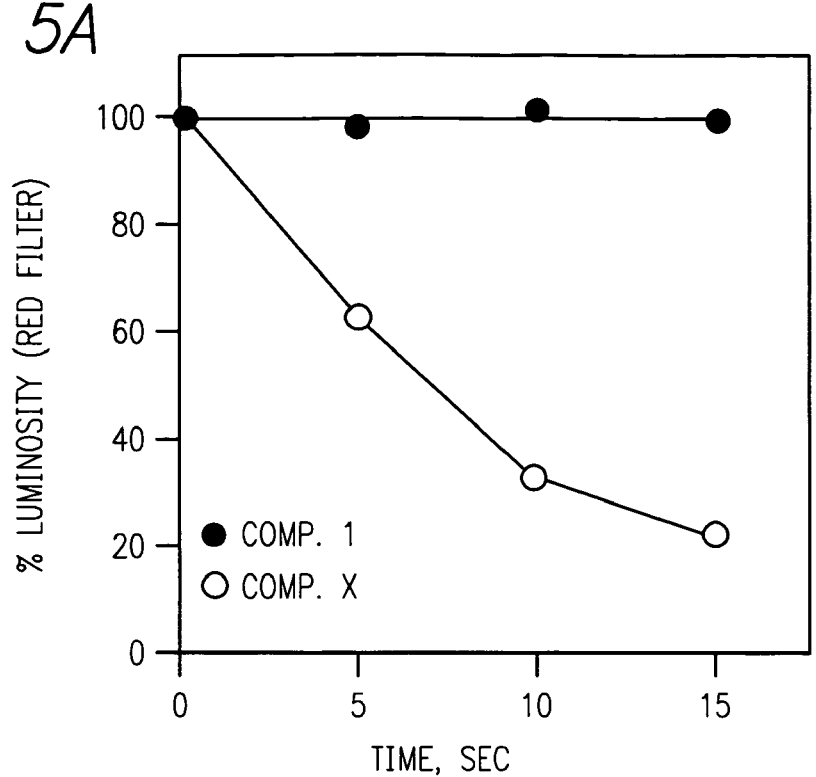
FIG. 5: Resistance of an anthraquinone fluorochrome to photo-bleaching and photo-conversion.
Figure 5B:
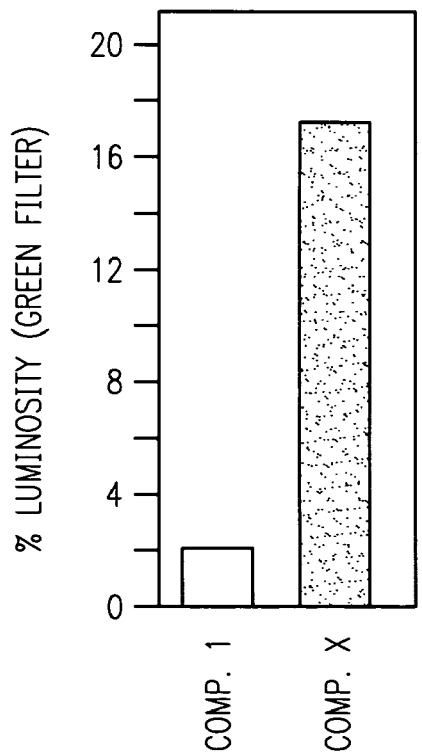

Despite long observation periods and long exposure times while imaging, the fluorescence of compound 1 does not fade away (FIG. 4, panel A). In contrast, LysoTracker Red rapidly photobleaches upon extended observation periods. Additionally, LysoTracker Red dye demonstrated photoconversion from a red to a green-emitting form, as previously reported (Freundt et al, 2007). This spurious signal was readily quantified in control HeLa cells and is depicted in FIG. 5$b$, relative to Compound 1.

Compound 1 is highly resistant to photobleaching relative to other dyes used for selectively labeling lysosomes. Compound 1 does not exhibit metachromasy, nor does it photoconvert to a green-emitting state, and is thus superior to acridine orange and Lysotracker Red for multi-color imaging in combination with GFP (Freundt et al, 2007; Nadrigny et al, 2007).

Example 26

Staining of Nuclei in Various Live Mammalian Cells, Using Compound 11

Figure 6:
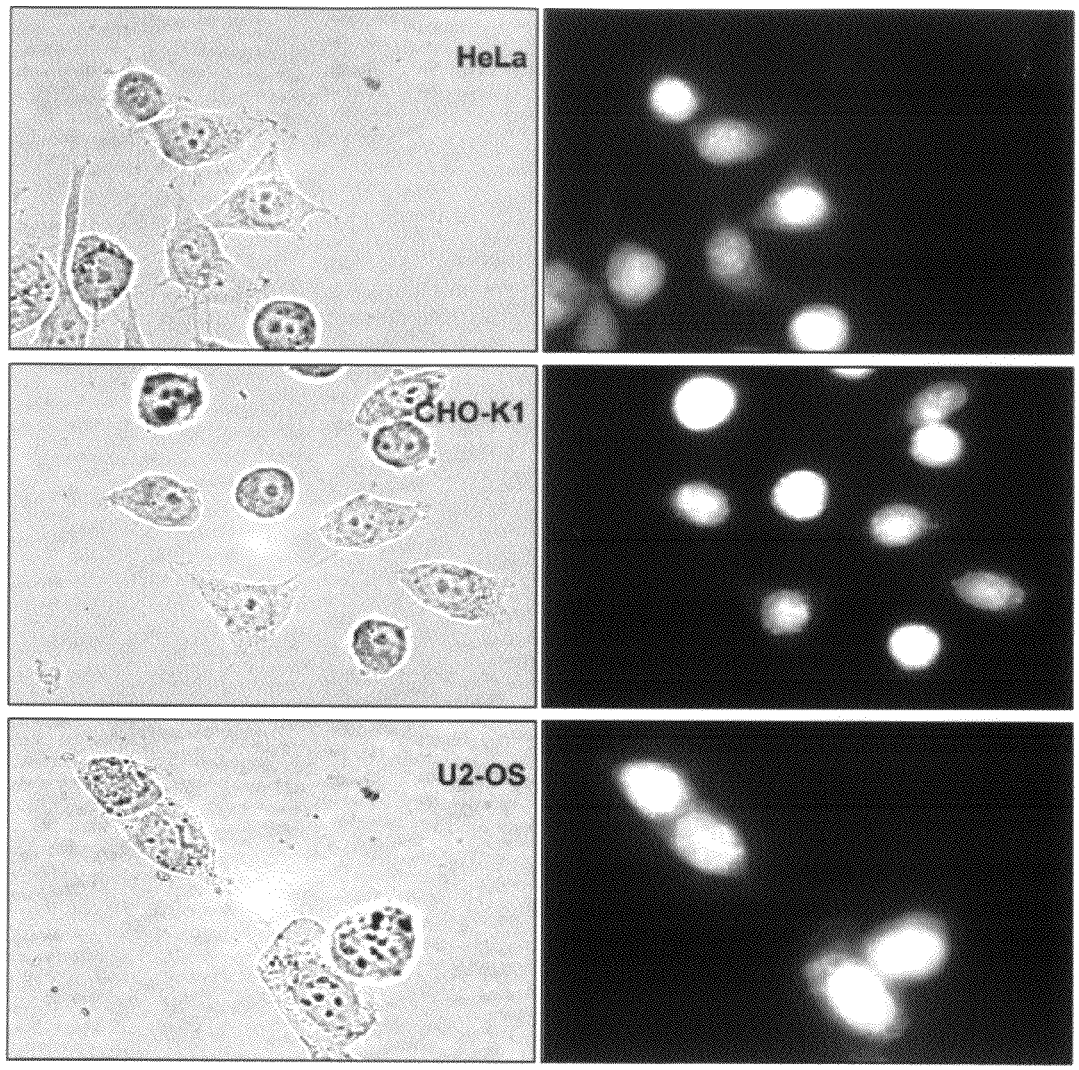
FIG. 6: Staining nuclei in various live mammalian cells with an anthraquinone fluorochrome.

The various mammalian cells were cultivated as described in example 17. After incubation of these cells with compound 11, as described in example 17, nuclei were imaged on an Olympus BX51 microscope (60× objective). CHO-K1 and U2-OS cells were incubated with various concentrations of Compound 11. At 100 µM some nuclear staining was observed, however 500 µM was optimum for staining nuclei after 15 min incubation at RT. As shown in FIG. 6, Compound 11 selectively accumulated on cell nuclei for all three mammalian cell lines evaluated. Similar experimental results were achieved using Compound 19. Lower concentrations of Compound 19 were required for staining of nuclei (10-20 µM) than for Compound 11 (~500 µM).

Example 27

Staining of Nuclei with Compound 11 in GFP-Expressing Cells

Figure 7:
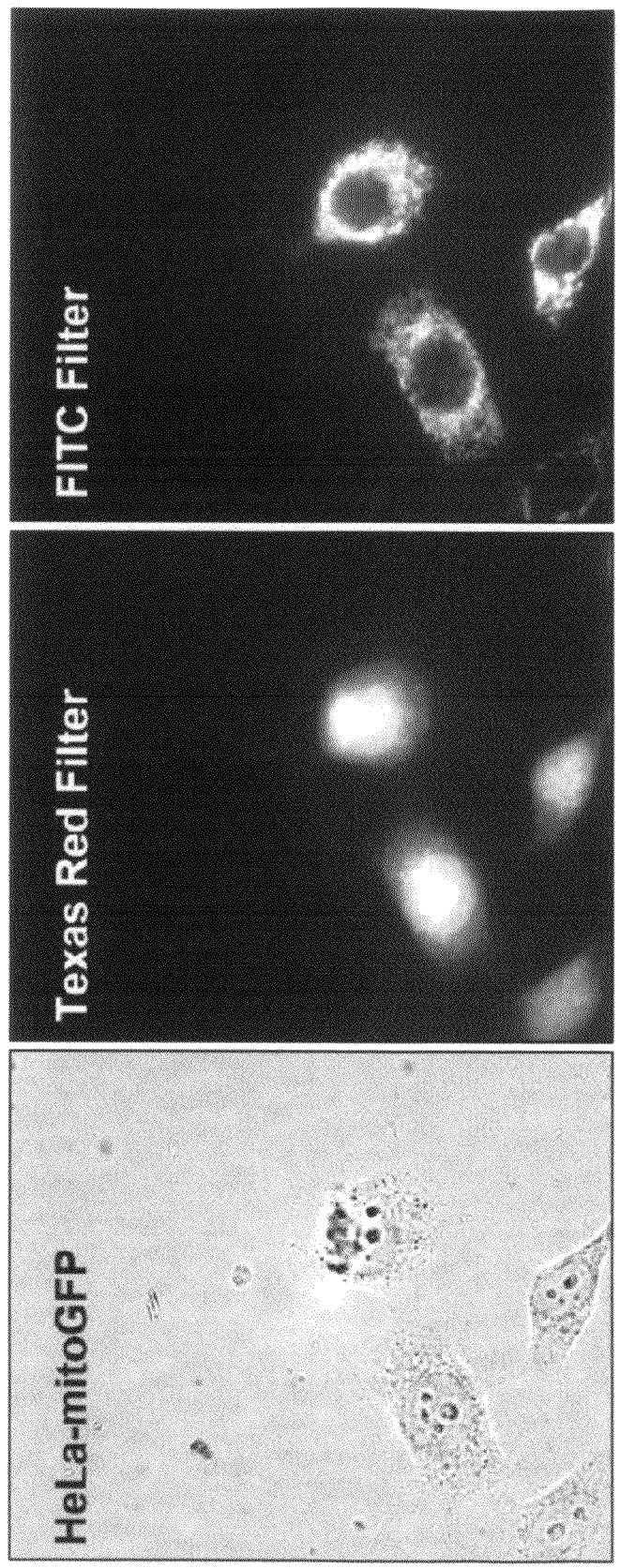
FIG. 7: Counter-staining nuclei in GFP-expressing cells with an anthraquinone fluorochrome.

The HeLa-TurboGreen-mitochondria (HeLa-mitoGFP, MarinPharm GmbH, Luckenwalde, Germany) cell line expresses EGFP-cytochrome oxidase chimeric proteins that are primarily localized to the mitochondria. The cells were cultivated as described in Example 12 for standard HeLa cells. After incubation of these cells with Compound 11, as described in Example 14, nuclei and mitochondria were independently imaged on an Olympus BX51 microscope (60× objective). Fluorescence signals from Compound 11 and GFP were readily distinguished using the Texas Red and FITC filters, as shown in FIG. 7. Control HeLa cells, not expressing GFP, displayed no fluorescence signal in the FITC window, while HeLa-mitoGFP cells, not treated with Compound 1, displayed no fluorescence signal in the Texas Red window. As with Compound 1, Compound 11 was not susceptible to photo-conversion to a green-emitting compound and exhibited excellent photostability relative to other commercially available nuclear stains. Additionally, the photostability was comparable to the anthraquinone-based dye, DRAQ5 (Biostatus Limited, Coventry, England).

Example 28

Simultaneous Detection of Nuclei, Lysosomes and Mitochondria Using Compound 1 and Hoechst 33342 Dye in Live GFP-Expressing Mammalian Cells One fundamental aspect of both flow cytometry and fluorescence microscopy is their ability to analyze and compare multiple cellular parameters simultaneously. In many instances, this requires that multiple dyes be loaded into a given set of cells. An important assumption in this type of work is that the various dyes do not interact with one another. However, previous efforts to simultaneously visualize nuclei and lysosomes in living cells has been compromised by observed incompatibilities between Draq5 and the Lysotracker family of dyes (Lysotracker Green DND 26 and Lysotracker Red DND 99, Invitrogen Corporation) (Snyder and Garon, 2003). When co-incubated with cells, the Draq5 nuclear stain almost completely inhibits uptake of the BODIPY dyes, possibly due to the two dyes complexing in solution into a form that is not taken up by cells. BODIPY-mycolactone is a fluorescent adduct of the macrolide produced by *Mycobacterium ulcerans*, a molecule known to localize to the cytoplasm of cells. Its entry into cells is also blocked by Draq5, suggesting that any BODIPY-based probe would be susceptible to this phenomenon. Although it would seem a simple matter to circumvent the observed dye interaction by adding the compounds sequentially with washing between steps, this too has led to problems. Regardless of whether the Lysotracker dye is incubated with cells prior to or after Draq5 labeling, minimal lysosomal labeling is observed.

Figure 8:
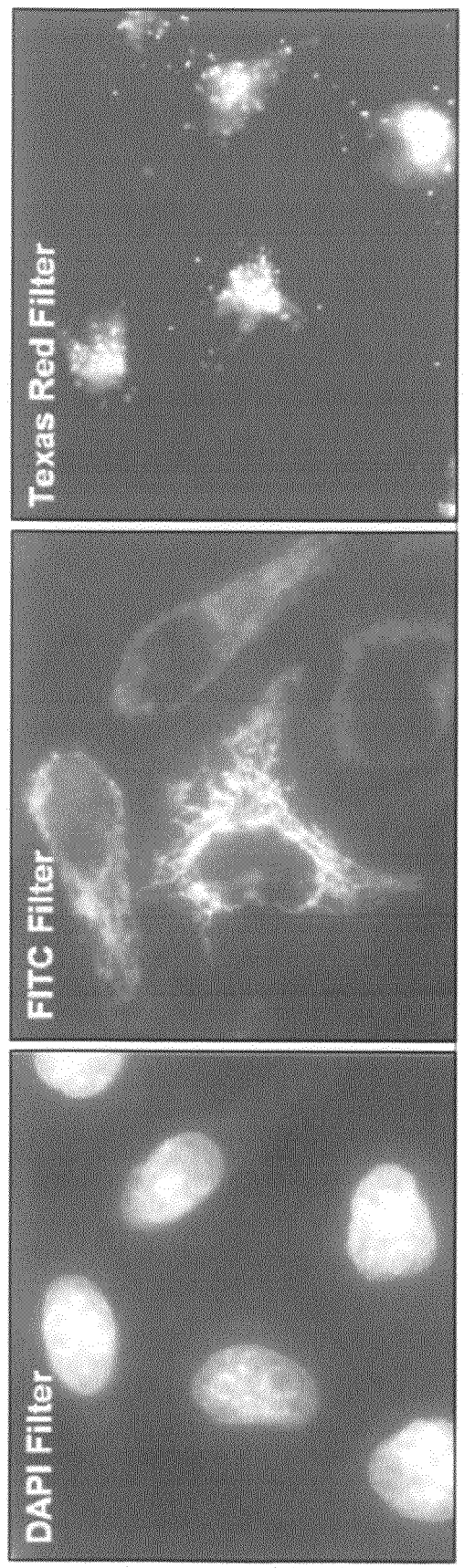
FIG. 8: Counter-staining lysosomes and nuclei in GFP-expressing cells with an anthraquinone fluorochrome and Hoechst 33258.

In order to achieve simultaneous labeling of nuclear, mitochondrial and lysosomal compartments in live cells, Compound 1 was prepared in combination with Hoechst 33342. The HeLa-TurboGreen-mitochondria (HeLa-mitoGFP, MarinPharm GmbH, Luckenwalde, Germany) cell line expresses EGFP-cytochrome oxidase chimeric proteins that are primarily localized to the mitochondria. The cells were cultivated as described in Example 12 for standard HeLa cells. After incubation of these cells with a mixture of Compound 1 and Hoechst 33342, nuclei, lysosomes and mitochondria were independently imaged on an Olympus BX51 microscope (60× objective). Fluorescence signals from Compound 1, GFP and Hoechst 33342 were readily distinguished using the Texas Red, FITC and DAPI filters, as shown in FIG. 8. No adverse interaction between Compound 1 and Hoechst 33342 dye was noted.

Example 29

Cytotoxicity of Compounds 10, 11 and 19 Toward HeLa Human Cervical Adenocarcinoma Cell Line Human cervical adenocarcinoma epithelial cell line HeLa was obtained from ATCC (ATTC, Manassas, Va.) and was routinely cultured in Dulbecco's modified eagle medium with low Glucose (Sigma-Aldrich, St. Louis, Mo.), supplemented with 10% fetal bovine serum heat inactivated (ATCC) and 100 U/ml penicillin, 100 µg/ml streptomycin (Sigma). Cell cultures were maintained in an incubator at 37° C., with 5% $CO_2$ atmosphere. Compound 10 was dissolved in DMSO to a 5 mM final stock concentration. Compound 11 was dissolved in 0.02 N HCl to a 20 mM final stock concentration. Compound 19 was dissolved in PBS to a 1 mM final stock concentration. Cytotoxicity of compounds 10, 11 and 19 was determined using standard MTT (3-(4,5-dimethyl-2-thiazolyl)-2,5-diphenyl-2H tetrazolium bromide) assay. The MTT assay is a laboratory test and a standard colorimetric assay (an assay which measures changes in color) for measuring the activity of enzymes that reduce MTT to formazan, giving a purple color. This mostly happens in mitochondria, and as such it is a measure of mitochondrial activity. The assay is typically used to determine cytotoxicity of potential medicinal agents and toxic materials.

For the cytotoxicity assay, HeLa cells were seeded in a 96 well plate at different densities ($10^3$, $5\times10^3$ and $10^4$ per well) and the next day were treated with serial dilutions of compounds 10, 11 or 19 in growth medium. Serial dilutions of compounds 10 and 11 were made in a range from 0.3 µM to 20 µM, compound 19 was tested in a range from 0.08 µM to 5 µM. Cells were incubated at 37° C. in a cell culture incubator 5% $CO_2$ atmosphere. The MTT assay was performed on day 1, 4 and 6 post treatment (for low cell density plates, $10^3$ cells/well) and on day 1 for plates with high cell density ($5\times10^3$ and $10^4$ per well). Growth media containing tested compounds was removed and 100 µL of fresh medium containing 0.5 mg/ml of MTT reagent was added to each well. Cells were incubated at 37° C. in a cell culture incubator 5% $CO_2$ atmosphere for 4 h, then 100 µL of solubilization solution (0.1N HCl in 10% SDS) was added to each well. After complete solubilization of the violet crystals (checked by microscope), optical density was read at 590 nm and cell viability was determined as a ratio of optical density of treated cells to optical density of untreated cells.

Figure 9:
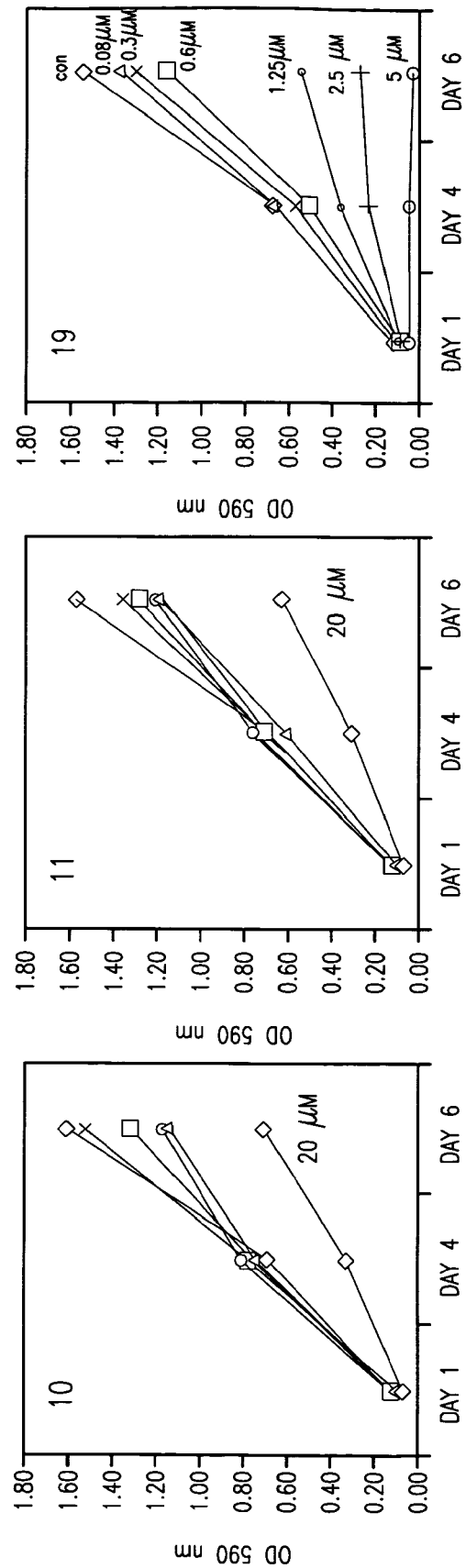
FIG. 9: Growth curves of HeLa cells treated with serial dilutions of anthraquinone-derived compounds.
Figure 10A:
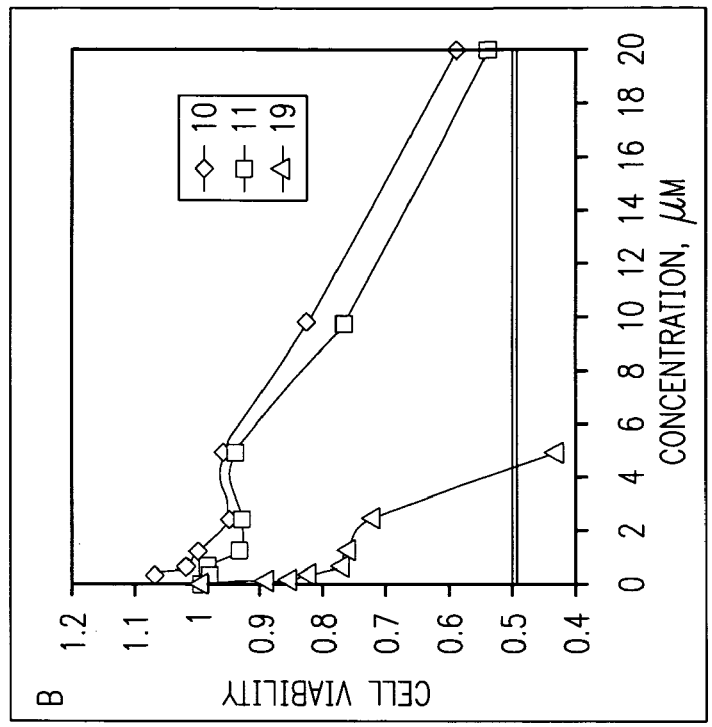
FIG. 10: Viability of the HeLa cells seeded at low and high density and treated with serial dilutions of anthraquinone-derived compounds.
Figure 10B:
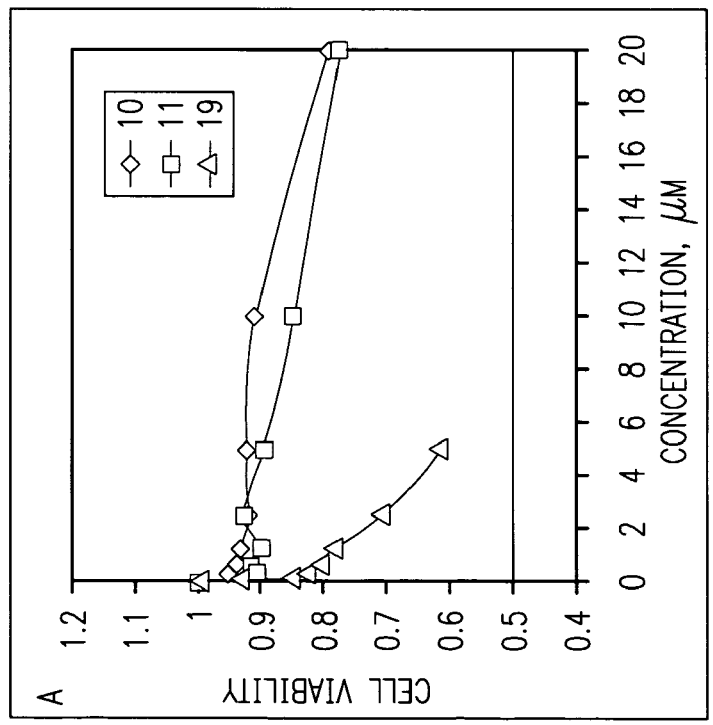

As demonstrated in FIG. 9, Compound 19 turned out to be the most cytotoxic of the three tested derivatives. For a 24 h incubation period, an IC50 of 5 µM for this compound was determined on low density HeLa cells. Two other compounds, 10 and 11, did not kill 50% of the cells during the 24 h period at concentrations tested. Experiments with HeLa cells seeded at low density were extended up to 6 days of treatment. Results of the extended experiment are presented in FIG. 10. Compound 10 and 11 exhibit slight concentration dependent growth suppressive effects (at concentrations higher than 5 µM). Only the highest concentration of compounds 10 and 11 (20 µM) had a significant growth suppressive effect on HeLa cells. However, HeLa cells treated even with the highest concentration of the compounds continue to grow. Over extended periods of time, compound 19 demonstrated a strong dose-dependent cytotoxic effect, and cells treated with this compound do not re-grow.

Example 30

Figure 11:
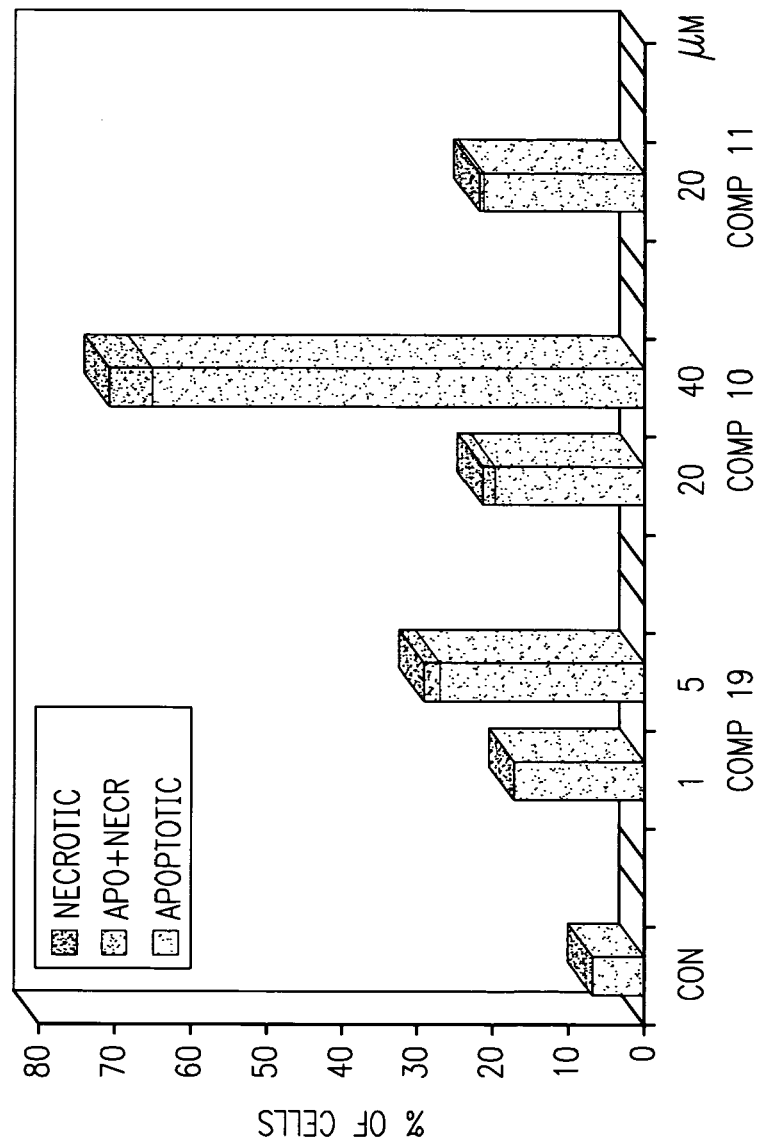
FIG. 11: Apoptosis induction in HeLa cells treated with anthraquinone-derived compounds.

Mitochondrial and Nuclear Localized Anthraquinone-Based Compounds 10, 11 and 19 Induced Apoptosis in HeLa Human Cervical Carcinoma Cell Line The human cervical adenocarcinoma HeLa cells were cultivated as described in example 25. An annexin V binding assay was utilized to detect apoptosis induction by anthraquinone-derived compounds 10, 11 and 19. The day before the experiment, HeLa cells were seeded in 6-well tissue culture plates at a density of $5\times10^6$ cells per well. The next day, the growth medium was removed from the wells and fresh medium containing different dilutions of compounds 10 (20 and 40 µM), 11 (20 µM) and 19 (1 and 5 µM) was added. Cells were incubated for three h in the cell culture incubator at 37° C. and 5% $CO_2$, washed with PBS, trypsinized, again washed twice with PBS and stained with Annexin V-FITC conjugate (Invitrogen, Carlsbad, Calif.) according to the manufacturer's instructions and analyzed using flow cytometry. To assess the cell membrane permeability, cells were counterstained with 10 µg/ml of 7-AAD just before the assay. FITC fluorescence was recorded in FL1 channel (filter 530/30 nm) and 7-AAD fluorescence was recorded in FL3 channel (670 LP filter). Cell debris were gated out and apoptosis was assessed by setting up quadrant gates using untreated cells as a control. Depending upon concentration, all tested compounds induced apoptosis in HeLa cells after 3 h treatment (FIG. 11). However, the range of apoptosis-inducing concentrations is much lower for compound 19. All tested compounds appeared to induce cell growth arrest at low concentrations, and apoptosis at higher concentrations, however the threshold for apoptosis induction is different for different compounds.

Many obvious variations will no doubt be suggested to those of ordinary skill in the art, in light of the above detailed description and examples of the present invention. It will be appreciated by those skilled in the art that any arrangement which is calculated to achieve the same purpose may be substituted for the specific embodiments shown. This application and invention are intended to cover any adaptations or variations of the present invention. All such variations are fully embraced by the scope and spirit of the invention as more particularly defined in the claims that now follow.

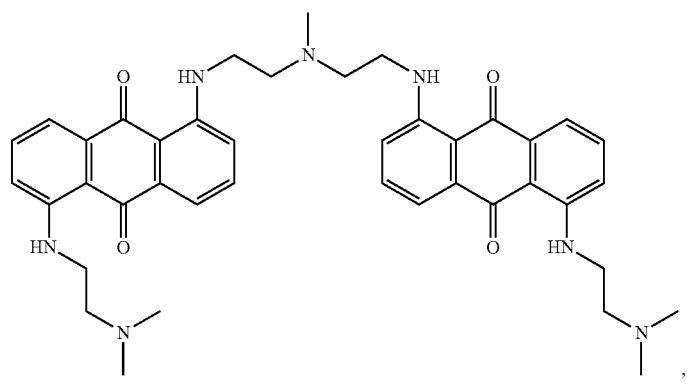

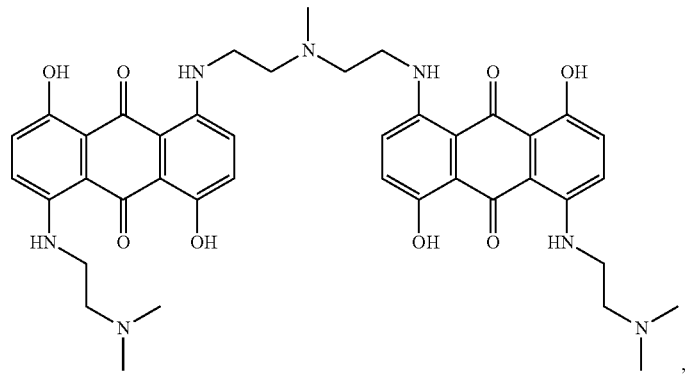

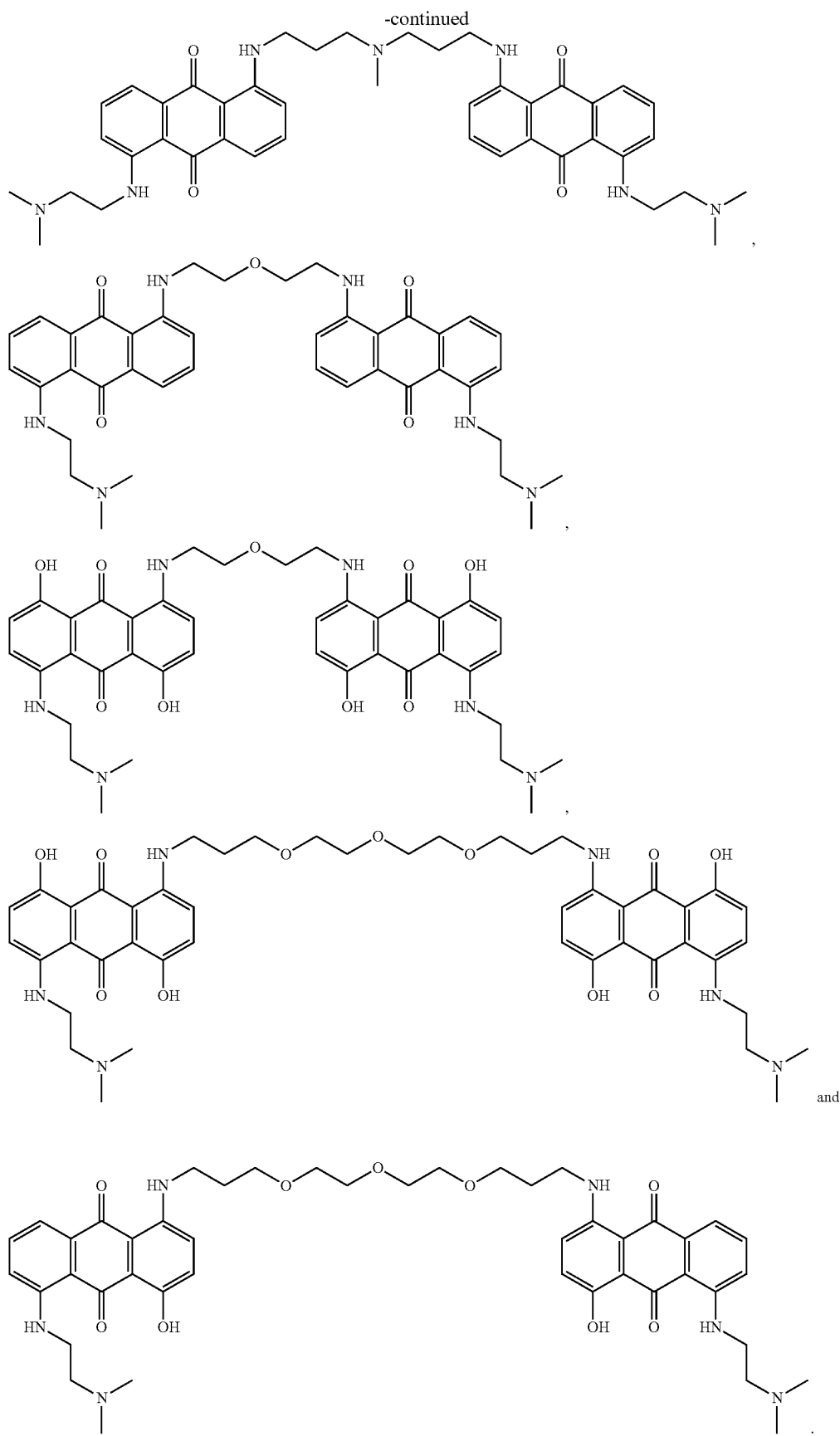

6. A compound selected from the group consisting of
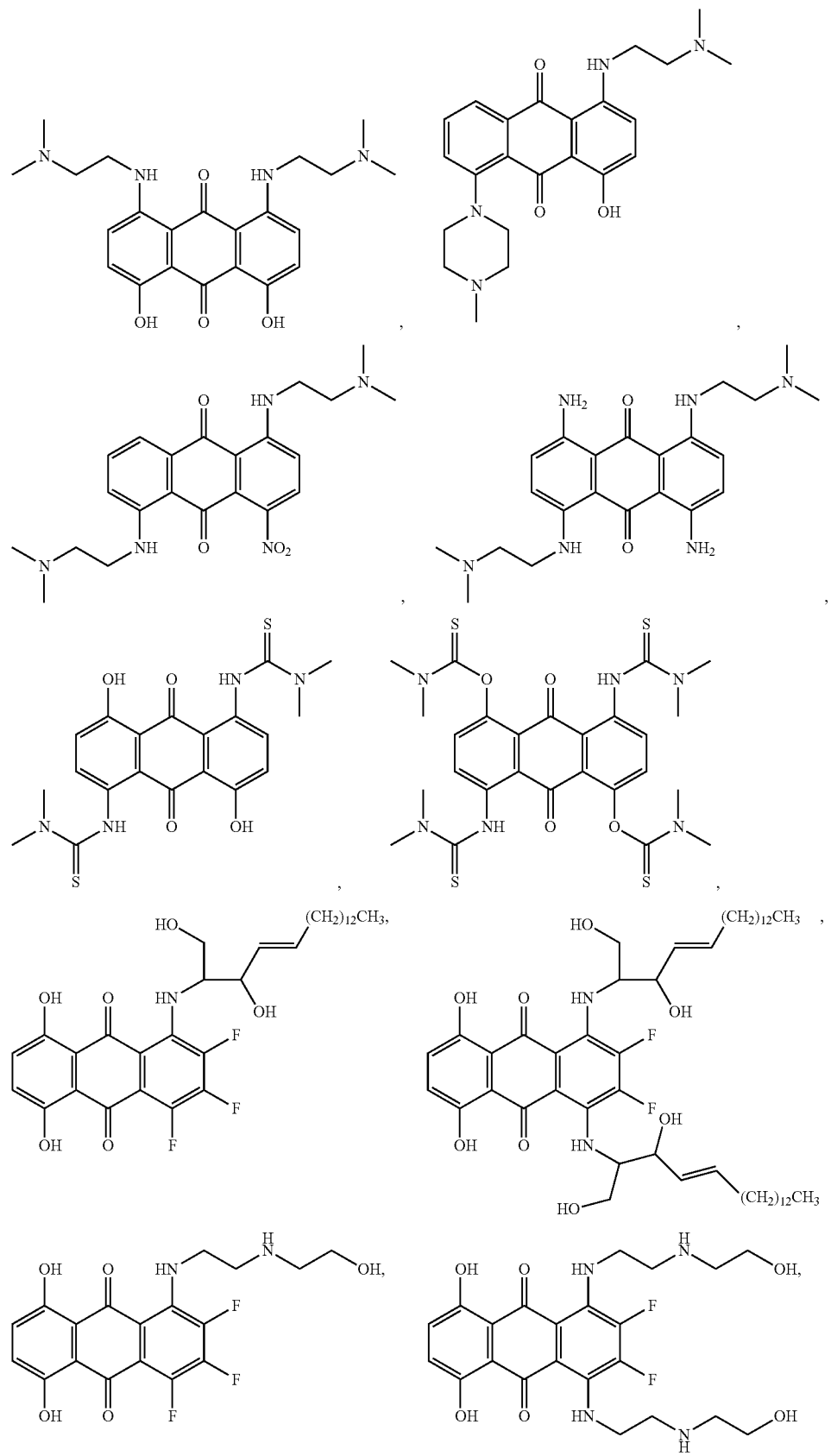

-continued
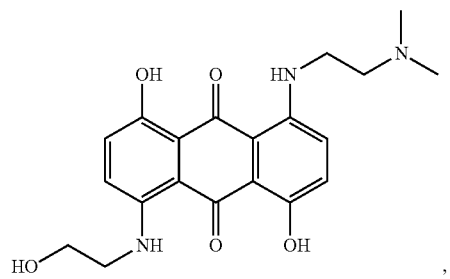
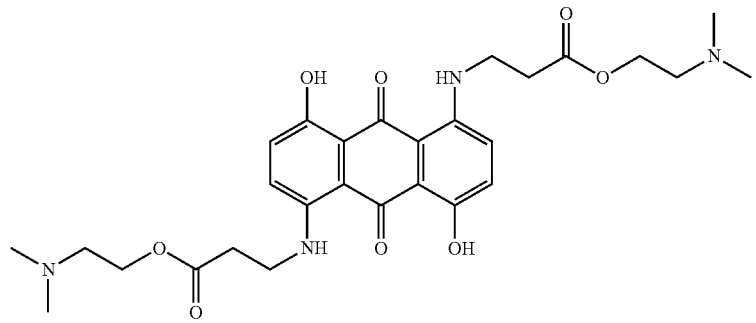
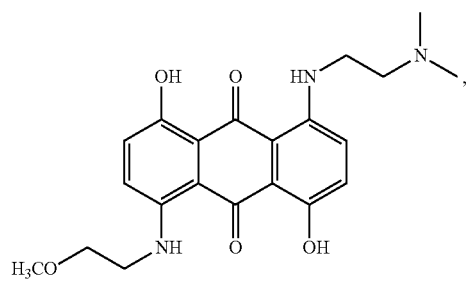
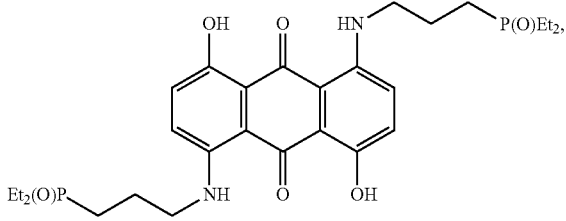
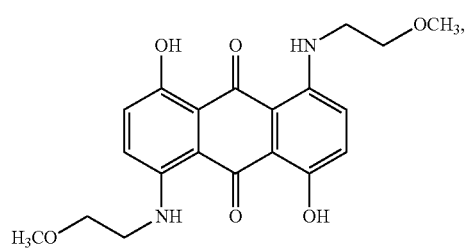
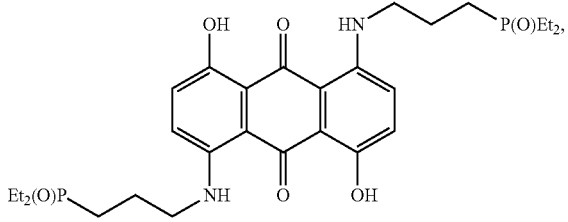
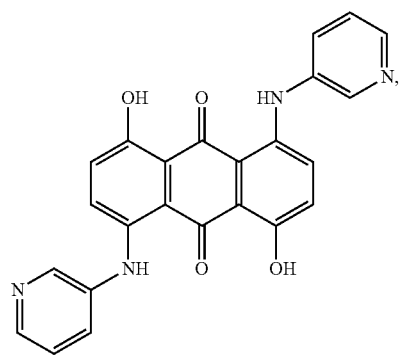

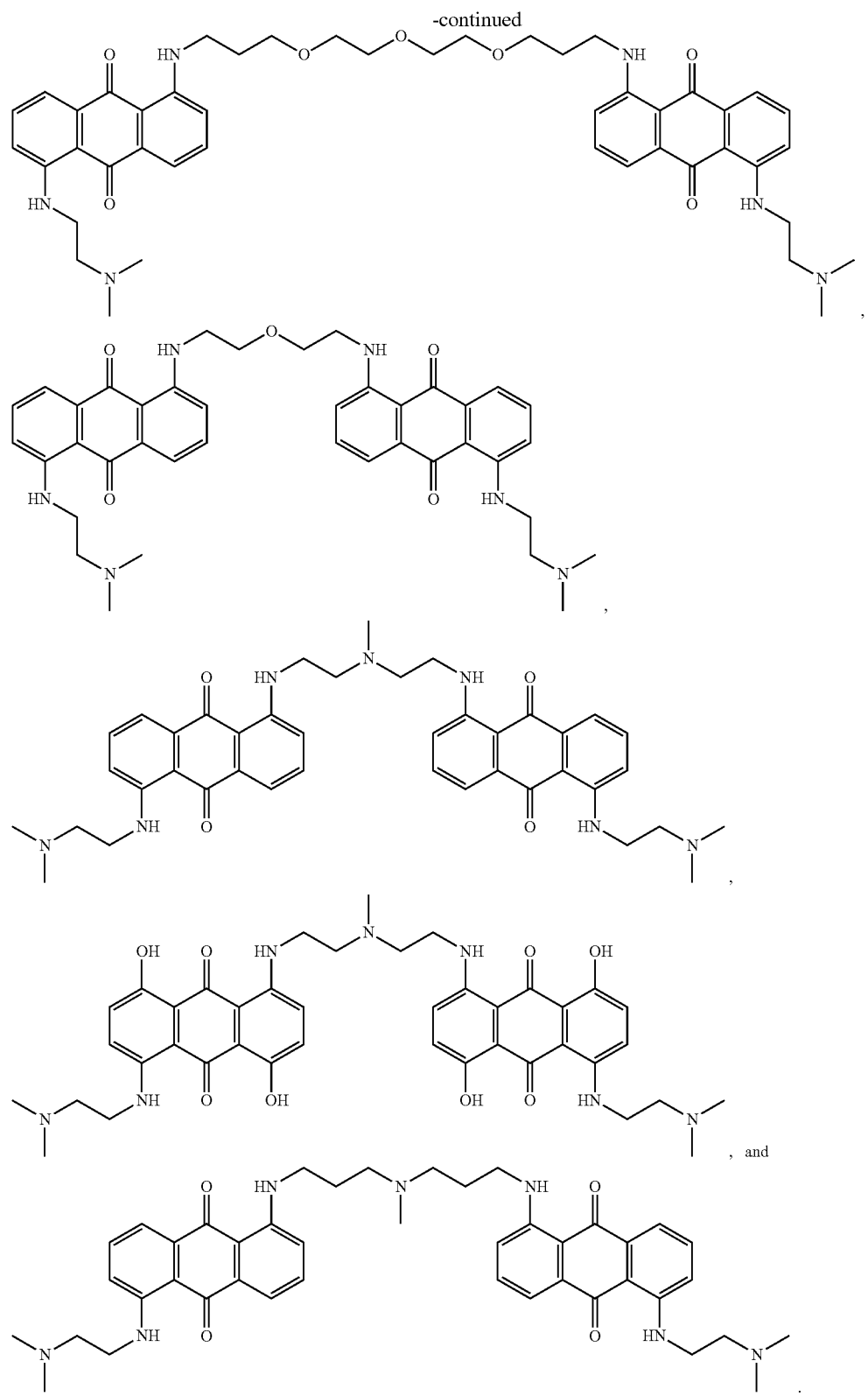

What is claimed is:

1. A compound selected from:

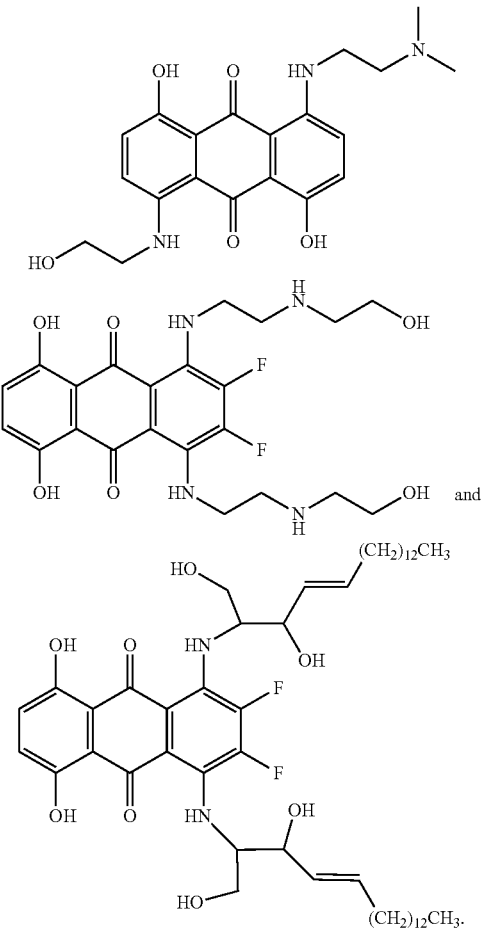

2. The compound having the structure

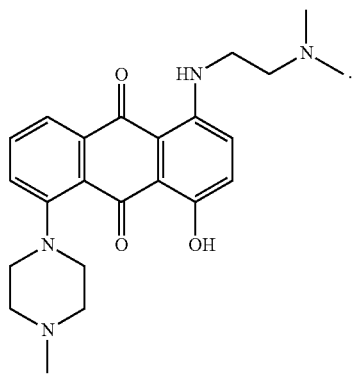 [SMILES: CN(C)CCNc1ccc(O)c2c1C(=O)c1cccc(N3CCN(C)CC3)c1C2=O]

3. A multimeric compound comprising two or more of the compounds of claim 1 or 2 joined together through a linkage group comprising a substituted or unsubstituted alkyl group, a substituted or unsubstituted alkenyl group, a substituted or unsubstituted heteroalkyl group, a substituted or unsubstituted heteroalkenyl group comprising an amide, or one or more substituted or unsubstituted aromatic rings.

4. A compound comprising two organelle-targeting fluorochrome compounds having the structure:

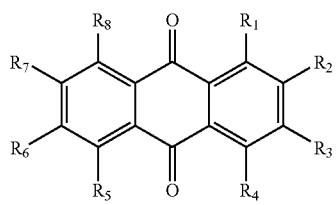

wherein $R_1$-$R_4$ and $R_5$-$R_8$ are independently selected from
H,
OH,
a halide,
a nitro group,
a substituted amine,
a CN group,
a charged group comprising a salt of an organic acid, an onium group or a protonated amine, wherein
said salt of an organic acid comprises a sulfate, a sulfonate, a phosphate, a phosphonate, a carboxylate, a borate, or a combination thereof, and
said onium group comprises a quaternary ammonium, a sulfonium, a phosphonium, or a combination thereof,
a substituted or unsubstituted alkyl or alkenyl group,
a substituted or unsubstituted amine, and
a thiourea group;
wherein only one member of $R_1$-$R_8$ comprises the structure NH-A-$R_aR_b$, wherein A is a $C_{2-8}$ alkylene group and $R_a$ and $R_b$ are independently selected from H, a $C_{1-4}$ alkyl, a $C_{2-4}$ hydroxyalkyl and a $C_{2-4}$ aminoalkyl; and wherein said two or more compounds are joined together through a linkage group comprising a substituted or unsubstituted alkyl group, a substituted or unsubstituted alkenyl group, a substituted or unsubstituted heteroalkyl group, a substituted or unsubstituted heteroalkenyl group comprising an amide, or one or more substituted or unsubstituted aromatic rings.

5. The compound of claim 4 selected from